(12) United States Patent
Chow et al.

(10) Patent No.: US 7,709,507 B2
(45) Date of Patent: *May 4, 2010

(54) THERAPEUTIC FLUOROETHYL UREAS

(75) Inventors: Ken Chow, Newport Coast, CA (US);
Wenkui K. Fang, Irvine, CA (US);
Evelyn G. Corpuz, Irvine, CA (US);
Daniel W. Gil, Corona Del Mar, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 434 days.

This patent is subject to a terminal disclaimer.

(21) Appl. No.: 11/747,181

(22) Filed: May 10, 2007

(65) Prior Publication Data

US 2007/0270498 A1 Nov. 22, 2007

Related U.S. Application Data

(60) Provisional application No. 60/747,444, filed on May 17, 2006.

(51) Int. Cl.
*A61K 31/381* (2006.01)
*C07D 213/02* (2006.01)
*C07D 333/10* (2006.01)

(52) U.S. Cl. .................. 514/357; 546/329; 546/332; 549/29; 549/76; 564/32; 564/47; 514/438

(58) Field of Classification Search .................. 546/329, 546/332; 549/29, 74, 76; 514/357, 438; 564/32, 47

See application file for complete search history.

(56) References Cited

FOREIGN PATENT DOCUMENTS

EP 068590 1/1983
WO WO01/78702 A2 10/2001

OTHER PUBLICATIONS

SciFinder Search, pp. 1-13.
SciFinder Search, pp. 1-20.
SciFinder Search, pp. 1-8.
Boyd, Robert E., "Alpha 2-Adrenergic Agonists as Analgesic Agents," XP-001008886, Exp. Opin. Ther. Patents, 2000, 10(1):1741-1748.

*Primary Examiner*—Golam M Shameem
(74) *Attorney, Agent, or Firm*—John E. Wurst; Allergan, Inc.

(57) ABSTRACT

Compounds of the formula

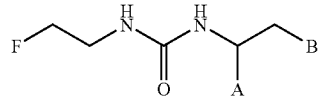

or a pharmaceutically acceptable salt thereof or a tautomer thereof, wherein A and B are as described herein, are useful for treating conditions afflicting mammals.

19 Claims, No Drawings

THERAPEUTIC FLUOROETHYL UREAS

CROSS-REFERENCE TO RELATED APPLICATION

This application claims the benefit of U.S. Provisional Application Ser. No. 60/747,444, filed May 17, 2006, which is hereby incorporated by reference in its entirety.

DESCRIPTION OF THE INVENTION

The compounds disclosed herein are agonists of alpha 2 adrenergic receptors in mammals. In particular, these compounds are useful for alleviating chronic pain, allodynia, muscle spasticity, diarrhea, neuropathic pain, visceral pain and other diseases and conditions.

One embodiment is a method comprising administering to a mammal a therapeutically effective amount of a compound for the treatment of chronic pain.

Another embodiment is a method comprising administering to a mammal a therapeutically effective amount of a compound for the treatment of allodynia.

Another embodiment is a method comprising administering to a mammal a therapeutically effective amount of a compound for the treatment of muscle spasticity.

Another embodiment is a method comprising administering to a mammal a therapeutically effective amount of a compound for the treatment of diarrhea.

Another embodiment is a method comprising administering to a mammal a therapeutically effective amount of a compound for the treatment of neuropathic pain.

Another embodiment is a method comprising administering to a mammal a therapeutically effective amount of a compound for the treatment of visceral pain.

One embodiment is use of a compound in the manufacture of a medicament for the treatment of chronic pain.

Another embodiment is use of a compound in the manufacture of a medicament for the treatment of allodynia.

Another embodiment is use of a compound in the manufacture of a medicament for the treatment of muscle spasticity.

Another embodiment is use of a compound in the manufacture of a medicament for the treatment of diarrhea.

Another embodiment is use of a compound in the manufacture of a medicament for the treatment of neuropathic pain.

Another embodiment is use of a compound in the manufacture of a medicament for the treatment of visceral pain.

Another embodiment is a medicament comprising a compound which is described hereafter.

Another embodiment is a dosage form comprising a compound which is described hereafter.

Another embodiment is a composition comprising a compound which is described hereafter.

For each of the embodiments disclosed above, an individual embodiment is contemplated for each description of a compound or a range of compounds identified hereafter.

Generally, the compounds useful herein are described by the formula

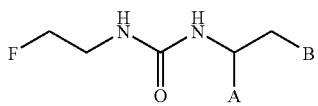

or a pharmaceutically acceptable salt thereof, a tautomer thereof, or a prodrug thereof;
wherein A is cycloalkyl, aryl, or heteroaryl;
A is a five-membered or six-membered monocyclic ring or a fused bicyclic thereof;
A is substituted or unsubstituted; and
if A is substituted, it has one or more stable substituents consisting of C, N, O, S, P, F, Cl, Br, and H; and each substituent has 1, 2, 3, or 4 atoms which are not hydrogen; and
B is aryl or heteroaryl,
B is a five-membered or six-membered monocyclic ring or a fused bicyclic thereof;
B is substituted or unsubstituted; and
if B is substituted, it has one or more stable substituents consisting of C, N, O, S, P, F, Cl, Br, and H; and each substituent has 1, 2, 3, or 4 atoms which are not hydrogen.

A is cycloalkyl, aryl, or heteroaryl. "Cycloalkyl" is a hydrocarbon ring that has no double bonds such as cyclohexane. "Aryl" is an unsubstituted or substituted aromatic ring or ring system such as phenyl, naphthyl, and the like. "Heteroaryl" is aryl having one or more N, O, or S atoms in the ring, i.e. one or more ring carbons are substituted by N, O, and/or S, such as pyridyl, thienyl, and the like.

A is also a five-membered or six-membered monocyclic ring or a fused bicyclic thereof. In other words A is a five-membered ring; A is a six-membered ring; or A is a fused bicyclic ring system having a five-membered ring fused to a five-membered ring, a six-membered ring fused to a five membered ring, or a six-membered ring fused to a six-membered ring. A fused bicyclic ring system is a bicyclic system where two atoms adjacent atoms on one ring also form to adjacent atoms on the other ring. Thus, the rings and ring systems shown below, or heterocyclic, aryl, or heteroaryl versions thereof, are contemplated.

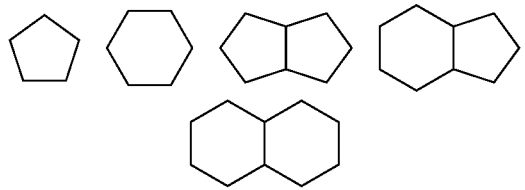

A is substituted or unsubstituted; if A is substituted, it has one or more stable substituents consisting of C, N, O, S, P, F, Cl, Br, and H; and each substituent has 1, 2, 3, or 4 atoms which are not hydrogen. A stable substituent is one which is sufficiently stable to render the compound as a whole effective for at least one of the uses, methods, or purposes disclosed herein. The total number of the C, N, O, S, P, F, Cl, and Br combined in the substituents is 1, 2, 3, or 4. For example $NO_2$ has 3 atoms which are not hydrogen, CN has 2 atoms which are not hydrogen, $NH_3$ has 1 atom which is not hydrogen, and $CO_2NHCH_3$ has 4 atoms which are not hydrogen.

Generally, those of ordinary skill in the art recognize stable substituents, examples include, but are not limited to:
hydrocarbyl, i.e. a moiety consisting of only carbon and hydrogen such as alkyl, alkenyl, alkynyl, and the like, including linear, branched or cyclic hydrocarbyl, and combinations thereof;
hydrocarbyloxy, meaning O-hydrocarbyl such as $OCH_3$, $OCH_2CH_3$, O-cyclohexyl, etc;
other ether substituents such as $CH_2OCH_3$, $CH_2OCH_2CH_3$, and the like;

thioether substituents including S-hydrocarbyl and other thioether substituents;

hydroxyhydrocarbyl, meaning hydrocarbyl-OH such as CH$_2$OH, CH$_2$CH$_2$OH, etc;

nitrogen substituents such as NO$_2$, CN, and the like, including amino, such as NH$_2$, NH(CH$_2$CH$_3$OH), NHCH$_3$, and the like;

carbonyl substituents, such as CO$_2$H, ester, amide, and the like;

halogen, such as chloro, fluoro, bromo, and the like fluorocarbyl, such as CF$_3$, etc.;

phosphorous substituents, such as PO$_3{}^{2-}$, and the like;

sulfur substituents, including S-hydrocarbyl having up to 3 carbon atoms, SH, SO$_3$H, SO$_2$CH$_3$, and the like.

The substituents on any given ring or ring system may be the same or different, and there may be as many substituents as the ring will bear. Thus, phenyl may have up to 5 substituents, naphthyl may have up to 7 substituents, thienyl may have up to 3 substituents, etc.

Thus, compounds of the formulas below are contemplated. Each structure, together with pharmaceutically acceptable salts of compounds of the structure, tautomers of compounds of the structure, and prodrugs of compounds of the structure, are individually contemplated embodiments.

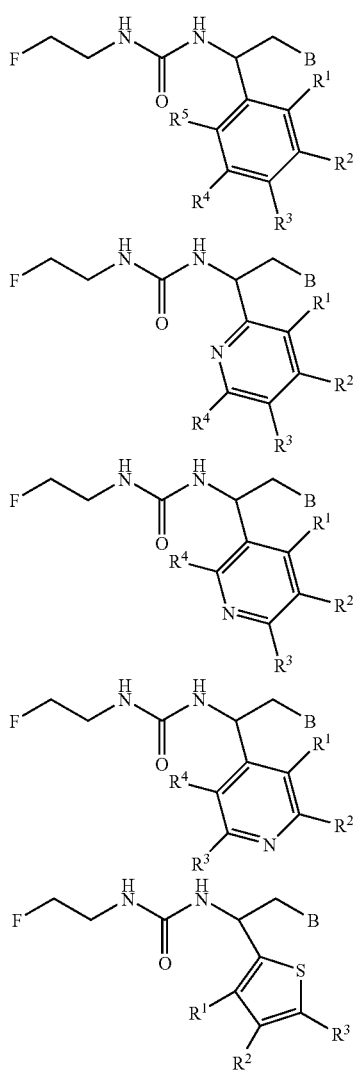

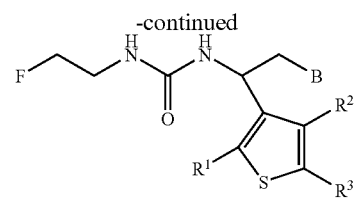

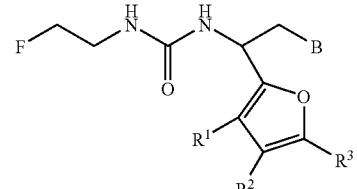

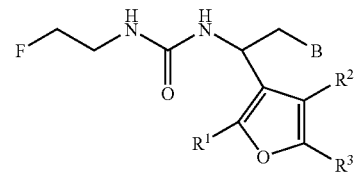

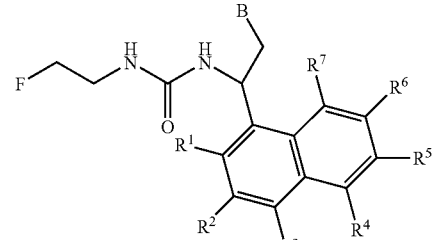

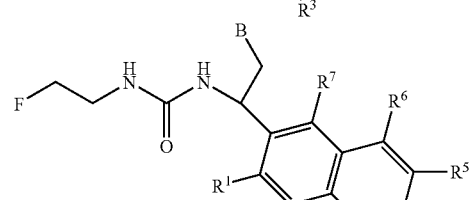

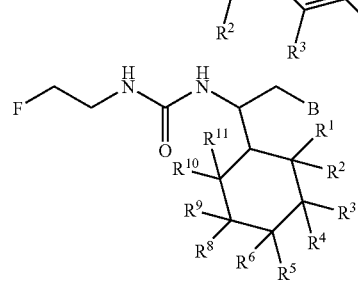

$R^1$, $R^2$, $R^3$, $R^4$, $R^5$, $R^6$, $R^7$, $R^8$, $R^9$, $R^{10}$, and $R^{11}$ are independently stable moieties consisting of C, N, O, S, P, F, Cl, Br, and H, which have 0, 1, 2, 3, or 4 atoms which are not hydrogen.

In another embodiment, $R^1$, $R^2$, $R^3$, $R^4$, $R^5$, $R^6$, $R^7$, $R^8$, $R^9$, $R^{10}$, and $R^{11}$ are independently Cl, F, CF$_3$, O-methyl, O-ethyl, O-n-propyl, O-isopropyl, Br, methyl, ethyl, n-propyl, isopropyl, n-butyl, sec-butyl, isobutyl, t-butyl, OH, or NO$_2$.

In another embodiment, $R^1$, $R^2$, $R^3$, $R^4$, $R^5$, $R^6$, $R^7$, $R^8$, $R^9$, $R^{10}$, and $R^{11}$ are independently Cl, F, CF$_3$, OCH$_3$, Br, CH$_3$, and OH.

B, including rings, ring systems, and substituents, may be anything that A may be subject to the constraint that B is aryl or heteroaryl. B and A may be the same or different in any given molecule.

Thus, compounds of the formulas below are contemplated. Each structure, together with pharmaceutically acceptable salts of compounds of the structure, tautomers of compounds of the structure, and prodrugs of compounds of the structure, are individually contemplated embodiments.

[Chemical structures shown]

$R^1$, $R^2$, $R^3$, $R^4$, and $R^5$ are independently stable moieties consisting of C, N, O, S, P, F, Cl, Br, and H, which have 0, 1, 2, 3, or 4 atoms which are not hydrogen.

In another embodiment, $R^1$, $R^2$, $R^3$, $R^4$, and $R^5$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

In another embodiment, $R^1$, $R^2$, $R^3$, $R^4$, and $R^5$ are independently Cl, F, $CF_3$, $OCH_3$, Br, $CH_3$, and OH.

In another embodiment, A is cyclohexyl.

In another embodiment, A is cyclopentyl.

In another embodiment, A is substituted or unsubstituted phenyl.

In another embodiment, A is substituted or unsubstituted thienyl.

In another embodiment, A is substituted or unsubstituted furyl.

In another embodiment, A is substituted or unsubstituted pyridinyl.

In another embodiment, A is substituted or unsubstituted naphthyl.

In another embodiment, A is cyclopentyl, cyclohexyl, substituted or unsubstituted aryl, or substituted or unsubstituted heteroaryl.

In one embodiment, A is substituted or unsubstituted phenyl and B is substituted or unsubstituted phenyl.

In another embodiment, A is cyclohexyl and B is substituted or unsubstituted phenyl.

In another embodiment, A is cyclopenty and B is substituted or unsubstituted phenyl.

In another embodiment A is substituted or unsubstituted thienyl and B is substituted or unsubstituted phenyl.

In another embodiment A is substituted or unsubstituted naphthyl and B is substituted or unsubstituted phenyl.

In another embodiment A is substituted or unsubstituted pyridinyl and B is substituted or unsubstituted phenyl.

In another embodiment, A is substituted or unsubstituted phenyl and B is substituted or unsubstituted pyridinyl.

In another embodiment, A is substituted or unsubstituted phenyl and B is substituted or unsubstituted thienyl.

In another embodiment A is substituted or unsubstituted furyl and B is substituted or unsubstituted phenyl.

In another embodiment, A is unsubstituted or is substituted with substitutents which are independently F, Cl, Br, I, CN, $SO_3H$, $NO_2$, $CF_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $CH(CH_3)_3$, cyclopropyl, methylcyclopropyl, cyclobutyl, OH, $OCH_3$, $OCH_2CH_3$, $OCH_2CH_2CH_3$, $OCH(CH_3)_2$, $SCH_3$, $SCH_2CH_3$, $SCH_2CH_2CH_3$, $SCH(CH_3)_2$, $NH_2$, $NCH_3$, $NCH_2CH_3$, $NCH_2CH_2CH_3$, $NCH(CH_3)_2$, $N(CH_3)_2$, $N(CH_3)(CH_2CH_3)$, $CO_2CH_3$, $CO_2CH_2CH_3$, $CONHCH_3$, $CONHCH_2CH_3$, or $CON(CH_3)_2$.

In another embodiment, A is unsubstituted or is substituted with substituents which are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

In another embodiment, A is unsubstituted or is substituted with substituents which are independently Cl, F, $CF_3$, $OCH_3$, Br, $CH_3$, or OH.

In another embodiment, B is substituted or unsubstituted phenyl.

In another embodiment, B is substituted or unsubstituted thienyl.

In another embodiment, B is substituted or unsubstituted furyl.

In another embodiment, B is substituted or unsubstituted pyridinyl.

In another embodiment, B is substituted or unsubstituted naphthyl.

In another embodiment, B is unsubstituted or is substituted with substitutents which are independently F, Cl, Br, I, CN, $SO_3H$, $NO_2$, $CF_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $CH(CH_3)_3$, cyclopropyl, methylcyclopropyl, cyclobutyl, OH, $OCH_3$, $OCH_2CH_3$, $OCH_2CH_2CH_3$, $OCH(CH_3)_2$, $SCH_3$, $SCH_2CH_3$, $SCH_2CH_2CH_3$, $SCH(CH_3)_2$, $NH_2$, $NCH_3$, $NCH_2CH_3$, $NCH_2CH_2CH_3$, $NCH(CH_3)_2$, $N(CH_3)_2$, $N(CH_3)(CH_2CH_3)$, $CO_2CH_3$, $CO_2CH_2CH_3$, $CONHCH_3$, $CONHCH_2CH_3$, or $CON(CH_3)_2$.

In another embodiment, B is unsubstituted or is substituted with substituents which are independently Cl, F, CF$_3$, O-methyl, O-ethyl, O-n-propyl, O-isopropyl, Br, methyl, ethyl, n-propyl, isopropyl, n-butyl, sec-butyl, isobutyl, t-butyl, OH, or NO$_2$.

In another embodiment, B is unsubstituted or is substituted with substituents which are independently Cl, F, CF$_3$, OCH$_3$, Br, CH$_3$, or OH.

The following compounds are specifically contemplated:
1-(1,2-diphenyl-ethyl)-3-(2-fluoro-ethyl)-urea;
1-[1-(3-chloro-phenyl)-2-phenyl-ethyl]-3-(2-fluoro-ethyl)-urea;
1-[1-(4-chloro-phenyl)-2-phenyl-ethyl]-3-(2-fluoro-ethyl)-urea;
1-(2-fluoro-ethyl)-3-[1-(3-fluoro-phenyl)-2-phenyl-ethyl]-urea;
1-(2-fluoro-ethyl)-3-[1-(3-methoxy-phenyl)-2-phenyl-ethyl]-urea;
1-(2-fluoro-ethyl)-3-[1-(4-fluoro-phenyl)-2-phenyl-ethyl]-urea;
1-[2-(2-Chloro-phenyl)-1-phenyl-ethyl]-3-(2-fluoro-ethyl)-urea;
1-(2-fluoro-ethyl)-3-[1-(2-fluoro-phenyl)-2-phenyl-ethyl]-urea;
1-(2-fluoroethyl)-3-[1-(4-methoxyphenyl)-2-phenylethyl]urea;
1-(2-fluoroethyl)-3-[1-(2-methoxyphenyl)-2-phenylethyl]urea;
1-[1-(3-Bromophenyl)-2-phenylethyl]-3-(2-fluoroethyl)urea;
1-(2-fluoroethyl)-3-[1-(4-methylphenyl)-2-phenylethyl]urea;
1-(2-fluoroethyl)-3-[1-(3-methylphenyl)-2-phenylethyl]urea;
1-[1-(3,4-dichlorophenyl)-2-phenylethyl]-3-(2-fluoroethyl)urea;
1-[1-(2-chlorophenyl)-2-phenylethyl]-3-(2-fluoroethyl)urea;
1-(1-cyclohexyl-2-phenylethyl)-3-(2-fluoroethyl)urea;
1-(1-cyclopentyl-2-phenylethyl)-3-(2-fluoroethyl)urea;
1-(2-fluoroethyl)-3-[2-(2-fluorophenyl)-1-phenylethyl]urea;
N-(2-fluoroethyl)-N'-[2-(3-fluorophenyl)-1-phenylethyl]urea;
1-(2-fluoroethyl)-3-[2-(4-fluorophenyl)-1-phenylethyl]urea;
1-[1-(3-chloro-2-fluorophenyl)-2-phenylethyl]-3-(2-fluoro-ethyl)urea;
1-(2-fluoroethyl)-3-[2-phenyl-1-(2-thienyl)ethyl]urea;
1-(2-fluoroethyl)-3-[1-(1-naphthyl)-2-phenylethyl]urea;
1-[1-(3-chlorophenyl)-2-(2-methylphenyl)ethyl]-3-(2-fluoroethyl)urea;
1-(2-fluoro-ethyl)-3-[2-(2-fluoro-phenyl)-1-m-tolyl-ethyl]-urea;
1-(2-fluoroethyl)-3-[2-(3-fluorophenyl)-1-m-tolylethyl]urea;
1-(2-fluoroethyl)-3-[2-(4-fluorophenyl)-1-m-tolylethyl]urea;
1-(2-fluoro-ethyl)-3-[1-(4-hydroxy-phenyl)-2-phenyl-ethyl]-urea;
1-[2-(2,5-difluoro-phenyl)-1-m-tolyl-ethyl]-3-(2-fluoro-ethyl)-urea;
1-[2-(2,3-difluoro-phenyl)-1-m-tolyl-ethyl]-3-(2-fluoro-ethyl)-urea;
1-(2-fluoro-ethyl)-3-[2-(2-fluoro-phenyl)-1-pyridin-3-yl-ethyl]-urea;
1-(2-fluoro-ethyl)-3-[2-(3-fluoro-phenyl)-1-pyridin-3-yl-ethyl]-urea;
1-(2-fluoro-ethyl)-3-[2-(4-fluoro-phenyl)-1-pyridin-3-yl-ethyl]-urea;
1-(2-fluoro-ethyl)-3-[2-(2-fluoro-phenyl)-1-pyridin-4-yl-ethyl]-urea;
1-[2-(3,4-difluoro-phenyl)-1-pyridin-4-yl-ethyl]-3-(2-fluoro-ethyl)-urea;
1-(2-fluoro-ethyl)-3-(2-pyridin-4-yl-1-m-tolyl-ethyl)-urea;
1-[1-(3-chloro-phenyl)-2-pyridin-4-yl-ethyl]-3-(2-fluoro-ethyl)-urea;
1-[2-(2,5-difluoro-phenyl)-1-pyridin-3-yl-ethyl]-3-(2-fluoro-ethyl)-urea;
1-(2-fluoro-ethyl)-3-(2-thiophen-2-yl-1-m-tolyl-ethyl)-urea;
1-(2-fluoro-ethyl)-3-(2-thiophen-2-yl-1-m-tolyl-ethyl)-urea;
1-[1-(3-chloro-phenyl)-2-m-tolyl-ethyl]-3-(2-fluoro-ethyl)-urea;
1-(2-fluoro-ethyl)-3-(1-furan-2-yl-2-phenyl-ethyl)-urea;
1-(2-fluoro-ethyl)-3-(2-pyridin-2-yl-1-m-tolyl-ethyl)-urea;
1-(2-fluoro-ethyl)-3-(2-pyridin-3-yl-1-m-tolyl-ethyl)-urea; and
1-(2-fluoro-ethyl)-3-[2-(3-fluoro-phenyl)-1-(3-trifluoromethyl-phenyl)-ethyl]-urea;

or a pharmaceutically acceptable salt, or a tautomer thereof.

The compounds disclosed herein may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

A tautomer is a compound which is in rapid equilibrium with another compound via transfer of a hydrogen, proton, or hydride ion. For example, tautomers of compounds depicted herein include, but are not necessarily limited to, those shown below.

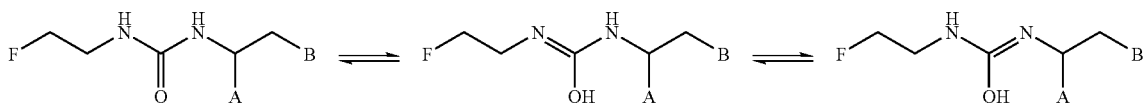

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Proton nuclear magnetic resonance ($^1$H NMR) and carbon nuclear magnetic resonance ($^{13}$C NMR) spectra were recorded on a Varian 300 or 500 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

GENERAL PROCEDURE A FOR THE SYNTHESIS OF FLUOROETHYL UREAS

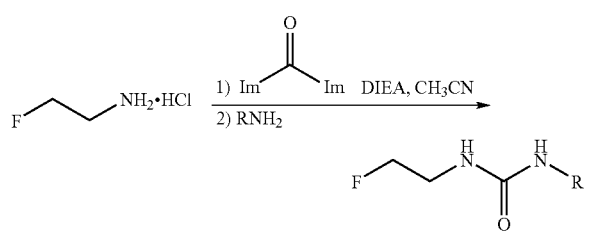

Fluoroethylamine hydrochloride (1.0 eq) was mixed with diimidazole carbonyl (1.0 eq) in acetonitrile at room temperature, and then diisopropylethyl amine (2.0 eq) was added. The resulting reaction mixture was stirred for 14 hours. An appropriate amine (1.0 eq) in acetonitrile was then added and the resulting mixture was stirred for another 14 hours. The reaction mixture was diluted with EtOAc and washed with H$_2$O (3×75 mL), then concentrated. Chromatography (gradient solvent system, from 50% EtOAc/hexanes to 10% Methanol/EtOAc) or recrystallization in CH$_3$CN gave the desired title compounds.

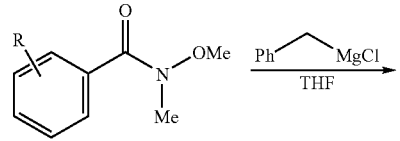

Synthesis of 1-(1,2-diphenyl-ethyl)-3-(2-fluoro-ethyl)-urea

The title compound was generated from commercially available 1,2-diphenyl-ethylamine according to general procedure A.

1-(1,2-Diphenyl-ethyl)-3-(2-fluoro-ethyl)-urea: The title compound was obtained from 1,2-diphenyl-ethylamine (2.00 g, 10.20 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 2.84-2.98 (m, 1H), 3.2 (q, J=5.6, 5.0 Hz, 1H), 3.3 (q, J=5.6, 5.0 Hz, 1H), 3.33-3.38 (m, 1H), 4.2 (t, J=5.0 Hz, 1H), 4.4 (t, J=5.0 Hz, 1H), 4.9 (q, J=7.9, 7.0 Hz, 1H), 6.1 (t, J=5.6 Hz, 1H), 6.5 (d, J=8.5 Hz, 1H), 7.07-7.37 (m, 10H).

General Procedure B for the Synthesis of Fluoroethyl Substituted 1,2-Diarylethyl Ureas:

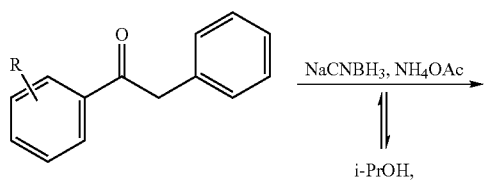

Et$_3$N (4.0 eq) was added to a mixture of an appropriately substituted benzoyl chloride, N, O-dimethyl-hydroxylamine (1.3 eq) and catalytic amount of DMAP in CH$_2$Cl$_2$ and the resulting mixture was stirred for 14 hours. Water was added to the reaction mixture, and the resulting mixture was extracted with EtOAc (3×200 mL). The combined organic extracts were washed with H$_2$O (2×200 mL), brine (1×200 mL), dried over MgSO$_4$ and concentrated to give the desired Weinreb's amide[1]. To a solution of this amide in THF at 0° C. was added appropriately substituted benzylmagnesium chloride (1.2 eq) and the resulting mixture was stirred for 3 hours. It was then quenched with 5% HCl and extracted with Et$_2$O (3×200 mL). The combined organic extracts were washed with H$_2$O (2×200 mL), brine (1×200 mL), dried over MgSO$_4$ and concentrated to give the desired ketone. This ketone was mixed with NaCNBH$_3$ (7.0 eq) and NH$_4$OAc (30 eq) in isopropanol and the desired diarylethylamine was produced according to the protocols as outlined in general procedure C. Alternatively, This ketone was mixed with methoxylamine hydrochloride (1.4 eq) in pyridine and was stirred for 14 hours. After concentration on a rotary evaporator, the residue washed with ether and the solvent was concentrated. The residue was dissolved in BH$_3$.THF (100 mL) and the resulting mixture was refluxed for 3 hours. After cooling the reaction mixture to room temperature then to 0° C., 20% NaOH was added and the resulting mixture was refluxed for 14 hours. After cooling to room temperature the reaction mixture was extracted with hexane and the combined organic extracts were dried with K$_2$CO$_3$ and concentrated to give the same desired diarylethylamine. The desired title urea was thus obtained according to the general procedure A described above.

[1] Nahm, S.; Weinreb, S. M. *Tet. Letters* 1981, 22, 3815-3818.

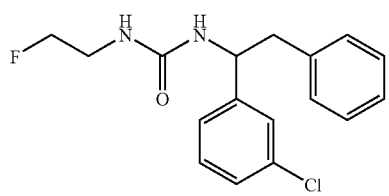

Synthesis of 1-[1-(3-chloro-phenyl)-2-phenyl-ethyl]-3-(2-fluoro-ethyl)-urea

The title compound was generated from commercially available 3-chloro-benzoyl chloride according to the general procedure B described above. The intermediates 3-chloro-N-methoxy-N-methyl-benzamide, 1-(3-chloro-phenyl)-2-phenyl-ethanone and 1-(3-chloro-phenyl)-2-phenyl-ethylamine were isolated and characterized.

3-Chloro-N-methoxy-N-methyl-benzamide[2]: The title amide was obtained from 3-chloro-benzoyl chloride (5.00 g, 28.60 mmol), N,O-dimethyl-hydroxylamine (3.50 g, 35.88 mmol) and catalytic amount of DMAP according to general procedure B described above. Spectroscopic data: $^1$H NMR (300 MHz, DMSO-d$_6$) δ ppm 3.24 (s, 3H) 3.52 (s, 3H) 7.52 (m, 4H).

[2] Gallagher, T. F.; et al. *Bioorganic Med. Chem.* 1997, 5, 49-64.

1-(3-Chloro-phenyl)-2-phenyl-ethanone[3]: The title ketone was obtained from 3-chloro-N-methoxy-N-methyl-benzamide (28.6 mmol) and benzylmagnesium chloride (17.00 mL, 2.0M in THF, 34.00 mmol) according to general procedure B described above.

[3] Jenkins, S. S. *J. Am. Chem. Soc.* 1933, 55, 703-706.

1-(3-Chloro-phenyl)-2-phenyl-ethylamine: The title compound was obtained from 1-(3-chloro-phenyl)-2-phenyl-ethanone (28.6 mmol), NaBH$_3$CN (13.60 g, 0.22 mol) and NH$_4$OAc (66.00 g, 0.86 mol) in isopropanol according to the protocols as outlined in general procedure B described above.

1-[1-(3-Chloro-phenyl)-2-phenyl-ethyl]-3-(2-fluoro-ethyl)-urea: The title urea was produced from 1-(3-chloro-phenyl)-2-phenyl-ethylamine (2.30 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 2.82-2.96 (m, 2H), 3.15 (q, J=5.3 Hz, 1H), 3.24 (q, J=5.3 Hz, 1H), 4.2 (t, J=5.0 Hz, 1H), 4.4 (t, J=5.3 Hz, 1H), 4.9 (q, J=7.9, 6.7 Hz, 1H), 6.1 (t, J=5.6 Hz, 1H), 6.6 (d, J=8.2 Hz, 1H), 7.07-7.37 (m, 9H).

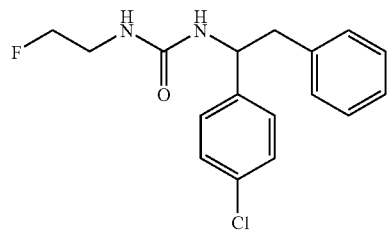

Synthesis of 1-[1-(4-chloro-phenyl)-2-phenyl-ethyl]-3-(2-fluoro-ethyl)-urea

The title compound was generated from commercially available 4-chloro-benzoyl chloride according to the general procedure B described above. The intermediates 4-chloro-N-methoxy-N-methyl-benzamide, 1-(4-chloro-phenyl)-2-phenyl-ethanone and 1-(4-chloro-phenyl)-2-phenyl-ethylamine were isolated and characterized.

4-Chloro-N-methoxy-N-methyl-benzamide[4]: The title amide was obtained from 4-chloro-benzoyl chloride (5.00 g, 28.60 mmol), N,O-dimethyl-hydroxylamine (3.50 g, 35.88 mmol), Et$_3$N (10.00 mL, 71.75 mmol) and catalytic amount of DMAP according to the protocols as outlined in general procedure B.

[4] Turnbull, K.; Sun, C.; Krein, D. M. *Tet. Letters* 1998, 39, 1509-1512.

1-(4-Chloro-phenyl)-2-phenyl-ethanone[5]: The title compound was obtained from 3-chloro-N-methoxy-N-methyl-benzamide (28.60 mmol) and benzylmagnesium chloride (17.00 mL, 2.0 M in THF, 34.00 mmol) according to the protocols as outlined in general procedure B.

[5] Jenkins, S. S.; Richardson, E. M. *J. Am. Chem. Soc.* 1933, 55, 1618-1621.

1-(4-Chloro-phenyl)-2-phenyl-ethylamine[6]: The title compound was obtained from 1-(4-chloro-phenyl)-2-phenyl-ethanone (28.60 mmol), NaBH$_3$CN (13.60 g, 0.22 mol) and NH$_4$OAc (66.00 g, 0.86 mol) according to the protocols as outlined in general procedure B described above.

[6] Gee, K. R.; et al. *J. Med. Chem.* 1993, 36, 1938-1946.

1-[1-(4-Chloro-phenyl)-2-phenyl-ethyl]-3-(2-fluoro-ethyl)-urea: The title urea was produced from 1-(4-chloro-phenyl)-2-phenyl-ethylamine (2.30 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: ¹H NMR (300 MHz, DMSO-$d_6$) δ 2.9 (d, J=7.3 Hz, 2H), 3.1 (q, J=5.3 Hz, 1H), 3.2 (q, J=5.0 Hz, 1H), 4.2 (t, J=5.0 Hz, 1H), 4.4 (t, J=5.0 Hz, 1H), 4.9 (q, J=7.6 Hz, 1H), 6.1 (t, J=5.3 Hz, 1H), 6.5 (d, J=8.2 Hz, 1H), 7.06-7.37 (m, 9H).

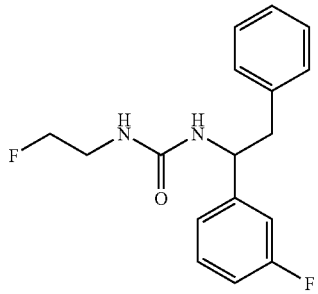

Synthesis of 1-(2-fluoro-ethyl)-3-[1-(3-fluoro-phenyl)-2-phenyl-ethyl]-urea

The title compound was generated from commercially available 3-fluoro-benzoyl chloride according to the general procedure B described above. The intermediates 3-fluoro-N-methoxy-N-methyl-benzamide, 1-(3-fluoro-phenyl)-2-phenyl-ethanone and 1-(3-fluoro-phenyl)-2-phenyl-ethylamine were isolated and characterized.

3-Fluoro-N-methoxy-N-methyl-benzamide: The title amide was obtained from 3-fluoro-benzoyl chloride (5.00 g, 31.50 mmol), N,O-dimethyl-hydroxylamine (4.00 g, 41.01 mmol), Et₃N (17.60 mL, 0.13 mol) and catalytic amount of DMAP according to the protocols as outlined in general procedure B.

1-(3-Floro-phenyl)-2-phenyl-ethanone[7]: The title ketone was obtained from 3-fluoro-N-methoxy-N-methyl-benzamide (31.5 mmol) and benzylmagnesium chloride (19.00 mL, 2.0 M in THF, 38.00 mmol) according to the protocols as outlined in general procedure B described above.

[7] Moffett, R. B.; Hester, J. B. *J. Med. Chem.* 1972, 15, 1243-1247.

1-(3-Fluoro-phenyl)-2-phenyl-ethylamine: The title amine was obtained from 1-(3-fluoro-phenyl)-2-phenyl-ethanone (31.50 mmol), methoxylamine hydrochloride (3.80 g, 45.50 mmol) and BH₃.THF (100.00 ml, 1.0 M in THF, 100.00 mmol) according to the general procedure B described above.

1-(2-Floro-ethyl)-3-[1-(3-fluoro-phenyl)-2-phenyl-ethyl]-urea: The title urea was obtained from 1-(3-fluoro-phenyl)-2-phenyl-ethylamine (2.20 g, 10.20 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: ¹H NMR (300 MHz, DMSO-$d_6$) δ 2.83-2.97 (m, 2H), 3.16 (q, J=5.3 Hz, 1H), 3.24 (q, J=5.3 Hz, 1H), 4.2 (t, J=5.0 Hz, 1H), 4.4 (t, J=5.0 Hz, 1H), 4.9 (q, J=8.2, 7.0 Hz, 1H), 6.1 (t, J=5.9 Hz, 1H), 6.5 (d, J=8.5 Hz, 1H), 6.94-7.39 (m, 9H).

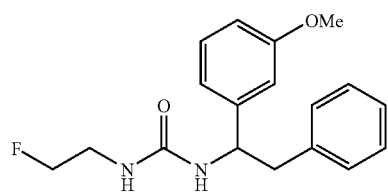

Synthesis of 1-(2-fluoro-ethyl)-3-[1-(3-methoxy-phenyl)-2-phenyl-ethyl]-urea

The title compound was generated from commercially available 3-methoxy-benzoyl chloride according to the general procedure B described above. The intermediates 3-methoxy-N-methoxy-N-methyl-benzamide, 1-(3-methoxy-phenyl)-2-phenyl-ethanone and 1-(3-methoxy-phenyl)-2-phenyl-ethylamine were isolated and characterized.

3-Methoxy-N-methoxy-N-methyl-benzamide[8]: The title compound was obtained from 3-methoxy-benzoyl chloride (5.00 g, 29.30 mmol), N,O-dimethyl-hydroxylamine (3.70 g, 37.93 mmol), Et₃N (16.40 mL, 0.12 mol) and catalytic amount of DMAP according to the protocols as outlined in general procedure B.

[8] Gallagher, Timothy F.; Seibel, George L.; Kassis, Shouki; Laydon, Jeffrey T.; Blumenthal, Mary Jane; et al.; BMECEP; Bioorg. Med. Chem.; EN; 5; 1; 1997; 49-64.

1-(3-Methoxy-phenyl)-2-phenyl-ethanone[9]: The title compound was obtained from 3-methoxy-N-methoxy-N-methyl-benzamide (29.30 mmol) and benzylmagnesium chloride (17.60 mL, 2.0 M in THF, 35.20 mmol) according to the protocols as outlined in general procedure B.

[9] Schneider, M. R.; von Angerer E.; Schonenberger, H.; Michel, R. Th.; Fortmeyer, H. P. *J. Med. Chem.* 1982, 25, 1070-1077.

1-(3-Methoxy-phenyl)-2-phenyl-ethylamine[10]: The title compound was obtained from 1-(3-methoxy-phenyl)-2-phenyl-ethanone (29.30 mmol), methoxylamine hydrochloride (3.40 g, 40.71 mmol) and BH₃.THF (100.00 mL, 1.0 M in THF, 100.00 mmol) according to the protocols as outlined in general procedure B.

[10] Clader, J. W.; et al. *J. Med. Chem.* 1995, 38, 1600-1607.

1-(2-Fluoro-ethyl)-3-[1-(3-methoxy-phenyl)-2-phenyl-ethyl]-urea: The title urea was produced from 1-(3-methoxy-phenyl)-2-phenyl-ethylamine (2.30 g, 10.10 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: ¹H NMR (300 MHz, DMSO-$d_6$) δ 2.82-2.96 (m, 2H), 3.2 (q, J=5.3 Hz, 1H), 3.3 (q, J=5.0 Hz, 1H), 3.7 (s, 3H), 4.2 (t, J=5.0 Hz, 1H), 4.4 (t, J=5.0 Hz, 1H), 4.9 (q, J=7.9, 7.0 Hz, 1H), 6.0 (t, J=5.9 Hz, 1H), 6.5 (d, J=8.5 Hz, 1H), 6.72-6.85 (m, 3H), 7.11-7.25 (m, 6H).

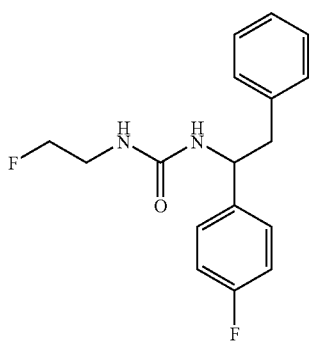

Synthesis of 1-(2-fluoro-ethyl)-3-[1-(4-fluoro-phenyl)-2-phenyl-ethyl]-urea

The title compound was generated from commercially available 4-fluoro-benzoyl chloride according to the general procedure B described above. The intermediates 4-fluoro-N-methoxy-N-methyl-benzamide, 1-(4-fluoro-phenyl)-2-phenyl-ethanone and 1-(4-fluoro-phenyl)-2-phenyl-ethylamine were isolated and characterized.

4-Fluoro-N-methoxy-N-methyl-benzamide[11]: The title compound was obtained from 4-fluoro-benzoyl chloride (5.00 g, 31.50 mmol), N,O-dimethyl-hydroxylamine (4.00 g, 41.01 mmol), Et$_3$N (17.60 mL, 0.13 mol) and catalytic amount of DMAP according to the protocols as outlined in general procedure B.

[11] Callahan, J. F.; et al. J. Med. Chem. 2002, 45, 999-1001.

1-(4-Floro-phenyl)-2-phenyl-ethanone[12]: The title compound was obtained from 4-fluoro-N-methoxy-N-methyl-benzamide (31.50 mmol) and benzylmagnesium chloride (19.00 mL, 2.0 M in THF, 38.00 mmol) according to the protocols as outlined in general procedure B.

[12] Hashimoto, H.; Imamura, K.; Haruta, J.; Wakitani, K. J. Med. Chem. 2002, 45, 1511-1517.

1-(4-Fluoro-phenyl)-2-phenyl-ethylamine[13]: The title compound was obtained from 1-(4-fluoro-phenyl)-2-phenyl-ethanone (31.50 mmol), methoxylamine hydrochloride (3.70 g, 37.93 mmol) and BH$_3$.THF (100 mL, 1.0 M in THF, 100.00 mmol) according to the protocols as outlined in general procedure B.

[13] Gyenes, F.; Bergmann, K. E.; Welch, J. T. J. Org. Chem. 1998, 63, 2824-2828.

1-(2-Floro-ethyl)-3-[1-(4-fluoro-phenyl)-2-phenyl-ethyl]-urea: The title compound was afforded from 1-(4-fluoro-phenyl)-2-phenyl-ethylamine (2.20 g, 10.20 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 2.9 (d, J=7.3 Hz, 2H), 3.2 (q, J=5.0 Hz, 1H), 3.3 (q, J=5.3 Hz, 1H), 4.2 (t, J=5.0 Hz, 1H), 4.4 (t, J=5.0 Hz, 1H), 4.9 (q, J=7.6 Hz, 1H), 6.1 (t, J=5.6 Hz, 1H), 6.5 (d, J=8.5 Hz, 1H), 7.03-7.35 (m, 9H).

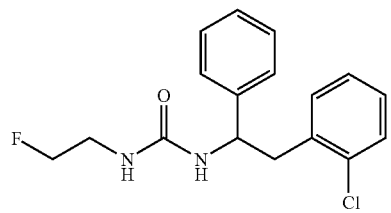

Synthesis of 1-[2-(2-Chloro-phenyl)-1-phenyl-ethyl]-3-(2-fluoro-ethyl)-urea

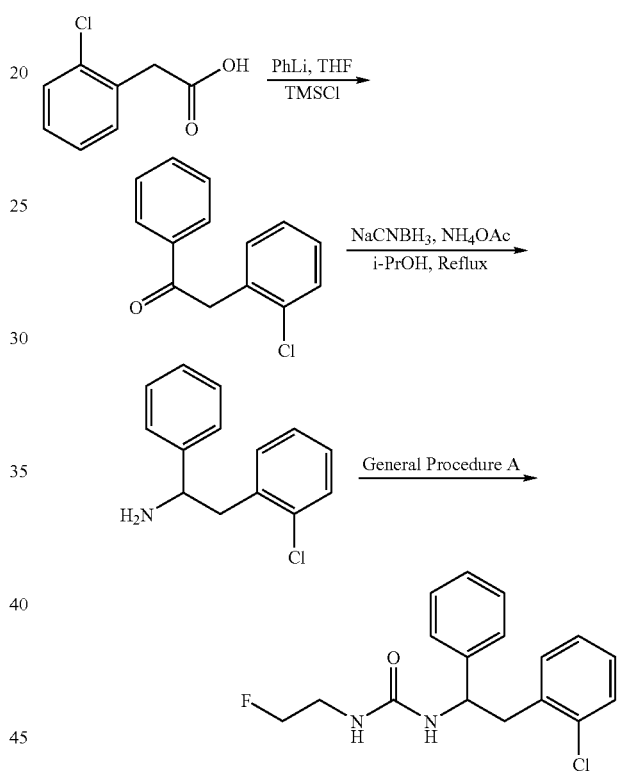

The title compound was generated from commercially available (2-chloro-phenyl)-acetic acid according to chemistry described above. The intermediates 2-(2-chloro-phenyl)-1-phenyl-ethanone and 2-(2-chloro-phenyl)-1-phenyl-ethylamine were isolated and characterized.

2-(2-Chloro-phenyl)-1-phenyl-ethanone[14]: Phenyl lithium (14.00 mL, 2.0 M in THF, 28.00 mmol) was added a solution of (2-chloro-phenyl)-acetic acid (5.00 g, 29.30 mmol) in THF at −78° C. and the resulting mixture was stirred for 3 hours. TMSCl (5.0 mL) was then added and the resulting mixture was diluted with ether, washed with aqueous K$_2$CO$_3$ (2×200 mL) and brine (1×200 mL), then dried over MgSO$_4$ and concentrated to give the title ketone.

[14] Cooper, D. J.; Owen, L. N. J. Chem. Soc. C 1966, 533-540.

2-(2-Chloro-phenyl)-1-phenyl-ethylamine: The title amine was obtained from 2-(2-Chloro-phenyl)-1-phenyl-ethanone (29.30 mmol), NaBH$_3$CN (13.00 g, 0.21 mol) and NH$_4$OAc (67.70 g, 0.88 mol) in isopropanol according to the protocols as outlined in general procedure B.

1-[2-(2-Chloro-phenyl)-1-phenyl-ethyl]-3-(2-fluoro-ethyl)-urea: The title urea was afforded from 2-(2-chloro-phenyl)-1-phenyl-ethylamine (2.30 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-$d_6$) δ 2.72-2.85 (m, 1H), 2.85-2.96 (m, 1H), 3.1 (q, J=5.3 Hz, 1H), 3.2 (q, J=5.3 Hz, 1H), 4.03-4.23 (m, 2H), 4.3 (t, J=5.3 Hz, 1H), 5.9 (t, J=5.9 Hz, 1H), 6.0 (d, J=8.8 Hz, 1H), 7.17-7.26 (m, 5H), 7.28-7.37 (m, 4H).

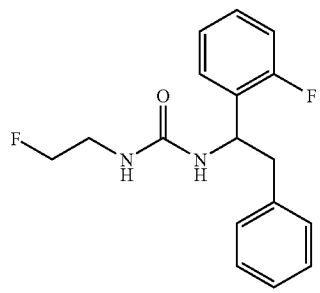

Synthesis of 1-(2-fluoro-ethyl)-3-[1-(2-fluoro-phenyl)-2-phenyl-ethyl]-urea

The title compound was generated from commercially available 2-fluoro-benzoyl chloride according to the general procedure B described above. The intermediates 2-fluoro-N-methoxy-N-methyl-benzamide, 1-(2-fluoro-phenyl)-2-phenyl-ethanone and 1-(2-fluoro-phenyl)-2-phenyl-ethylamine were isolated and characterized.

2-Fluoro-N-methoxy-N-methyl-benzamide: The title amide was obtained from 3-fluoro-benzoyl chloride (10.0 g, 63.07 mmol), N,O-dimethyl-hydroxylamine (7.60 g, 77.91 mmol), Et$_3$N (32.00 mL, 0.23 mol) and catalytic amount of DMAP according to the protocols as outlined in general procedure B.

1-(2-Floro-phenyl)-2-phenyl-ethanone[15]: The title ketone was obtained from 2-fluoro-N-methoxy-N-methyl-benzamide (63.00 mmol) and benzylmagnesium chloride (2.0 M in THF, 40.00 mL, 80.00 mmol) according to the protocols as outlined in general procedure B described above. Spectroscopic data: $^1$H NMR (300 MHz, DMSO-$d_6$) δ ppm 4.30 (d, J=2.35 Hz, 2 H) 7.19-7.34 (m, 7 H) 7.55-7.69 (m, 1 H) 7.85 (td, J=7.77, 1.76 Hz, 1 H).
[15] Anstead, Gregory M.; Peterson, Chad S.; Pinney, Kevin G.; Wilson, Scott R.; Katzenellenbogen, John A. J. Med. Chem. 1990, 33, 2726-2734.

1-(2-Fluoro-phenyl)-2-phenyl-ethylamine: The title amine was obtained from 1-(2-fluoro-phenyl)-2-phenyl-ethanone (60.00 mmol, crude), methoxylamine hydrochloride (6.25 g, 74.83 mmol) and BH$_3$.THF (100.00 ml, 1.0 M in THF, 0.10 mol) according to the general procedure B described above.

1-(2-Fluoroethyl)-3-[1-(2-fluorophenyl)-2-phenylethyl]urea: The title urea was obtained from 1-(2-fluoro-phenyl)-2-phenyl-ethylamine (taken from the previous step without further purification), diimidazole carbonyl (1.85 g, 11.40 mmol), fluoroethyl amine hydrochloride (1.24 g, 90% purity, 11.22 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.91 (d, J=7.33 Hz, 2 H) 3.16 (q, J=5.28 Hz, 1 H) 3.25 (q, J=5.28 Hz, 1 H) 4.22 (t, J=4.98 Hz, 1 H) 4.38 (t, J=4.98 Hz, 1H) 4.98-5.29 (m, 1 H) 6.14 (t, J=5.72 Hz, 1 H) 6.59 (d, J=8.80 Hz, 1 H) 6.96-7.41 (m, 9 H).

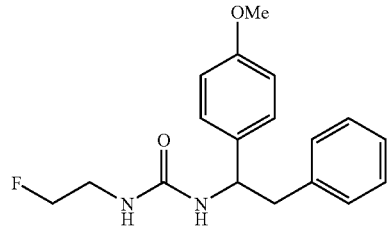

Synthesis of 1-(2-fluoroethyl)-3-[1-(4-methoxyphenyl)-2-phenylethyl]urea

The title compound was generated from commercially available 4-methoxy-benzoyl chloride according to the general procedure B described above. The intermediates 4-methoxy-N-methoxy-N-methyl-benzamide, 1-(4-methoxy-phenyl)-2-phenyl-ethanone and 1-(4-methoxy-phenyl)-2-phenyl-ethylamine were isolated and characterized.

4-Methoxy-N-methoxy-N-methyl-benzamide[16]: The title amide was obtained from 4-methoxy-benzoyl chloride (5.00 g, 29.34 mmol), N,O-dimethyl-hydroxylamine (3.50 g, 35.88 mmol), Et$_3$N (16.00 mL, 0.11 mol) and catalytic amount of DMAP according to the protocols as outlined in general procedure B. Spectroscopic data: $^1$H NMR (300 MHz, DMSO-$d_6$) δ ppm 3.21 (s, 3 H) 3.50 (s, 3 H) 3.77 (s, 3 H) 6.97 (s, 2 H) 7.60 (s, 2 H).
[16] Turnbull, Kenneth; Sun, Congcong; Krein, Douglas M. Tetrahedron Lett. 1998, 39, 1509-1512.

1-(4-Methoxy-phenyl)-2-phenyl-ethanone[17]: The title ketone was obtained from 4-methoxy-N-methoxy-N-methyl-benzamide (29.34 mmol, crude) and benzylmagnesium chloride (2.0 M in THF, 20.00 mL, 40.00 mmol) according to the protocols as outlined in general procedure B described above. Spectroscopic data: $^1$H NMR (300 MHz, DMSO-$d_6$) δ ppm 3.81 (s, 3 H) 4.29 (s, 2 H) 6.94-7.06 (m, 2 H) 7.17-7.31 (m, 5 H) 7.95-8.04 (m, 2 H).
[17] Jenkins J. Am. Chem. Soc. 1932, 54, 1155-1161.

1-(4-Methoxy-phenyl)-2-phenyl-ethylamine[18]: The title amine was obtained from 1-(4-methoxy-phenyl)-2-phenyl-ethanone (29.34 mmol, crude), methoxylamine hydrochloride (3.80 g, 45.50 mmol) and BH$_3$.THF (1.0 M in THF, 60.00 mL, 60.00 mmol) according to the general procedure B described above. Spectroscopic data: $^1$H NMR (300 MHz, DMSO-$d_6$) δ ppm 3.69 (s, 3 H) 3.98 (t, J=6.89 Hz, 1 H) 6.75-6.85 (m, 2 H) 7.04-7.16 (m, 3 H) 7.18-7.31 (m, 4 H).
[18] Gee, Kyle R.; Barmettler, Peter; Rhodes, Michael R.; McBurney, Robert N.; Reddy, N. Laxma; et al. J. Med. Chem. 1993, 36, 1938-1946.

1-(2-Fluoroethyl)-3-[1-(4-methoxyphenyl)-2-phenylethyl]urea: The title urea was obtained from 1-(4-methoxyphenyl)-2-phenyl-ethylamine (taken from the previous step without further purification), diimidazole carbonyl (1.95 g, 12.02 mmol), fluoroethyl amine hydrochloride (1.30 g, 90% purity, 11.76 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.90 (d, J=7.33 Hz, 2 H) 3.16 (q, J=5.28 Hz, 1 H) 3.26 (q, J=5.28 Hz, 1 H) 3.70 (s, 3 H) 4.22 (t, J=4.98 Hz, 1 H) 4.38 (t, J=5.13 Hz, 1 H) 4.82 (q, J=7.62 Hz, 1 H) 6.03 (t, J=5.72 Hz, 1 H) 6.43 (d, J=8.50 Hz, 1 H) 6.83 (d, J=8.50 Hz, 2 H) 7.09-7.23 (m, 7 H).

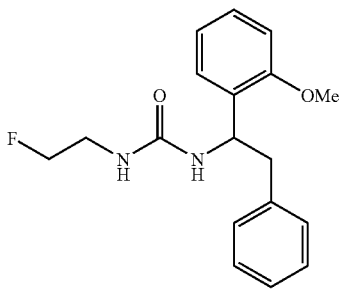

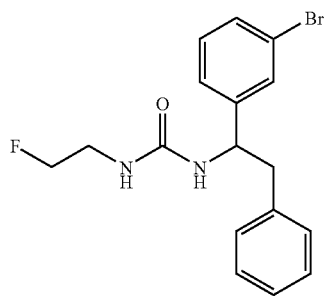

Synthesis of 1-(2-fluoroethyl)-3-[1-(2-methoxyphenyl)-2-phenylethyl]urea

The title compound was generated from commercially available 2-methoxy-benzoyl chloride according to the general procedure B described above. The intermediates 2-methoxy-N-methoxy-N-methyl-benzamide, 1-(2-methoxy-phenyl)-2-phenyl-ethanone and 1-(2-methoxy-phenyl)-2-phenyl-ethylamine were isolated and characterized.

2-Methoxy-N-methoxy-N-methyl-benzamide[19]: The title amide was obtained from 2-methoxy-benzoyl chloride (5.00 g, 29.34 mmol), N, O-dimethyl-hydroxylamine (3.50 g, 35.88 mmol), Et$_3$N (16.00 mL, 0.11 mol) and catalytic amount of DMAP according to the protocols as outlined in general procedure B.
[19] Gallagher, Timothy F.; Seibel, George L.; Kassis, Shouki; Laydon, Jeffrey T.; Blumenthal, Mary Jane; et al. Bioorg. Med. Chem. 1997, 5, 49-64.

1-(2-Methoxy-phenyl)-2-phenyl-ethanone[20]: The title ketone was obtained from 2-methoxy-N-methoxy-N-methyl-benzamide (29.34 mmol, crude) and benzylmagnesium chloride (2.0 M in THF, 17.00 mL, 34.00 mmol) according to the protocols as outlined in general procedure B described above. Spectroscopic data: $^1$H NMR (300 MHz, DMSO-d$_6$) δ ppm 3.90 (s, 3 H) 4.26 (s, 2 H) 7.01 (t, J=7.48 Hz, 1 H) 7.18-7.31 (m, 6 H) 7.42-7.56(m, 2 H).
[20] Kawase et al. Bull. Chem. Soc. Jpn. 1958, 31, 691.

1-(2-Methoxy-phenyl)-2-phenyl-ethylamine[21]: The title amine was obtained from 1-(2-methoxy-phenyl)-2-phenyl-ethanone (3.50 g, 15.40 mmol, crude), methoxylamine hydrochloride (3.50 g, 41.91 mmol) and BH$_3$.THF (1.0 M in THF, 60.00 mL, 60.00 mmol) according to the general procedure B described above.
[21] Clader, John W.; Berger, Joel G.; Burrier, Robert E.; Davis, Harry R.; Domalski, Martin; et al. J. Med. Chem. 1995, 38, 1600-1607.

1-(2-Fluoroethyl)-3-[1-(2-methoxyphenyl)-2-phenyl-ethyl]urea: The title urea was obtained from 1-(2-methoxyphenyl)-2-phenyl-ethylamine (taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.72 (dd, J=13.63, 8.65 Hz, 1 H) 2.92 (dd, J=13.49, 5.28 Hz, 1 H) 3.15 (q, J=5.28 Hz, 1 H) 3.24 (q, J=5.18 Hz, 1 H) 3.79 (s, 3 H) 4.21 (t, J=5.13 Hz, 1 H) 4.37 (t, J=4.98 Hz, 1 H) 5.15 (td, J=8.72, 5.42 Hz, 1 H) 6.15 (t, J=5.72 Hz, 1 H) 6.42 (d, J=9.09 Hz, 1 H) 6.86 (t, J=7.48 Hz, 1 H) 6.95 (d, J=8.21 Hz, 1 H) 7.08 (d, J=7.04 Hz, 3 H) 7.13-7.24 (m, 4 H).

Synthesis of 1-[1-(3-Bromophenyl)-2-phenylethyl]-3-(2-fluoroethyl)urea

The title compound was generated from commercially available 3-bromo-benzoyl chloride according to the general procedure B described above. The intermediates 3-bromo-N-methoxy-N-methyl-benzamide, 1-(3-bromo-phenyl)-2-phenyl-ethanone and 1-(3-bromo-phenyl)-2-phenyl-ethylamine were isolated and characterized.

3-Bromo-N-methoxy-N-methyl-benzamide: The title amide was obtained from 3-bromo-benzoyl chloride (5.00 g, 22.78 mmol), N,O-dimethyl-hydroxylamine (3.50 g, 35.88 mmol), Et$_3$N (16.00 mL, 0.11 mol) and catalytic amount of DMAP according to the protocols as outlined in general procedure B. Spectroscopic data: $^1$H NMR (300 MHz, DMSO-d$_6$) δ ppm 3.24 (s, 3 H) 3.52 (s, 3 H) 7.40 (t, J=7.77 Hz, 1 H) 7.57 (d, J=7.62 Hz, 1 H) 7.68 (d, J=7.92 Hz, 1 H) 7.70-7.73 (m, 1 H).

1-(3-Bromo-phenyl)-2-phenyl-ethanone[22]: The title ketone was obtained from 3-bromo-N-methoxy-N-methyl-benzamide (22.78 mmol, crude) and benzylmagnesium chloride (2.0 M in THF, 20.00 mL, 40.00 mmol) according to the protocols as outlined in general procedure B described above. Spectroscopic data: $^1$H NMR (300 MHz, DMSO-d$_6$) δ ppm 4.42 (s, 2 H) 7.19-7.35 (m, 4 H) 7.39-7.54 (m, 1 H) 7.84 (none, 1 H) 8.05 (none, 1 H) 8.18 (none, 1 H).
[22] Christy, M. E. et al. J. Med. Chem. 1977, 20, 421-430.

1-(3-Bromo-phenyl)-2-phenyl-ethylamine: The title amine was obtained from 1-(3-bromo-phenyl)-2-phenyl-ethanone (22.78 mmol, crude), methoxylamine hydrochloride (3.50 g, 41.91 mmol) and BH$_3$.THF (1.0 M in THF, 60.00 mL, 60.00 mmol) according to the general procedure B described above. Spectroscopic data: $^1$H NMR (500 MHz, DMSO-d$_6$) δ ppm 2.73-2.86 (m, 2 H) 4.07 (t, J=7.33 Hz, 1 H) 7.11-7.19 (m, 2 H) 7.21-7.31 (m, 3 H) 7.35-7.40 (m, 3 H) 7.55 (s, 1 H).

1-[1-(3-Bromophenyl)-2-phenylethyl]-3-(2-fluoroethyl) urea: The title urea was obtained from 1-(3-bromo-phenyl)-2-phenyl-ethylamine (taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (500 MHz, DMSO-d$_6$) δ ppm 2.86-2.95 (m, 2H) 3.18 (q, J=5.21 Hz, 1 H) 3.24 (q, J=5.37 Hz, 1 H) 4.26 (t, J=5.13 Hz, 1 H) 4.35 (t, J=5.13 Hz, 1 H) 4.85-4.90 (m, 1 H) 6.10 (t, J=5.86 Hz, 1 H) 6.57 (d, J=8.30 Hz, 1 H) 7.17 (t, J=7.81 Hz, 3 H) 7.22-7.28 (m, 4 H) 7.39 (dt, J=4.39, 2.20 Hz, 1 H) 7.46 (s, 1 H).

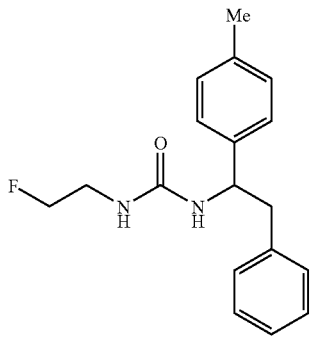

Synthesis of 1-(2-fluoroethyl)-3-[1-(4-methylphenyl)-2-phenylethyl]urea

The title compound was generated from commercially available 4-methyl-benzoyl chloride according to the general procedure B described above. The intermediates 4-methyl-N-methoxy-N-methyl-benzamide, 1-(4-methyl-phenyl)-2-phenyl-ethanone and 1-(4-methyl-phenyl)-2-phenyl-ethylamine were isolated and characterized.

4-Methyl-N-methoxy-N-methyl-benzamide[23]: The title amide was obtained from 4-methyl-benzoyl chloride (5.00 g, 32.34 mmol), N,O-dimethyl-hydroxylamine (3.50 g, 35.88 mmol), Et$_3$N (16.00 mL, 0.11 mol) and catalytic amount of DMAP according to the protocols as outlined in general procedure B.

[23] Turnbull, Kenneth; Sun, Congcong; Krein, Douglas M. *Tetrahedron Lett.* 1998, 39, 1509-1512.

1-(4-Methyl-phenyl)-2-phenyl-ethanone[24]: The title ketone was obtained from 4-methyl-N-methoxy-N-methyl-benzamide (32.34 mmol, crude) and benzylmagnesium chloride (2.0 M in THF, 18.00 mL, 36.00 mmol) according to the protocols as outlined in general procedure B described above. Spectroscopic data: $^1$H NMR (300 MHz, DMSO-d$_6$) δ ppm 2.35 (s, 3 H) 4.32 (s, 2 H) 7.20 (s, 8 H) 7.21-7.33 (m, 8 H) 7.93 (d, J=8.21 Hz, 1 H).

[24] Karaman, Rafik; Fry, James L. *Tetrahedron Lett.* 1990, 31, 941-944.

1-(4-Methyl-phenyl)-2-phenyl-ethylamine[25]: The title amine was obtained from 1-(4-methyl-phenyl)-2-phenyl-ethanone (32.34 mmol, crude), methoxylamine hydrochloride (3.50 g, 41.91 mmol) and BH$_3$.THF (1.0 M in THF, 60.00 mL, 60.00 mmol) according to the general procedure B described above. Spectroscopic data: $^1$H NMR (300 MHz, DMSO-d$_6$) δ ppm 2.24 (s, 3 H) 2.70-2.86 (m, 2 H) 3.98 (t, J=7.03 Hz, 1 H) 7.03-7.13 (m, 5 H) 7.15-7.21 (m, 4 H).

[25] Gyenes, Ferenc; Bergmann, Kathryn E.; Welch, John T. *J. Org. Chem.* 1998, 63, 2824-2828.

1-(2-Fluoroethyl)-3-[1-(4-methylphenyl)-2-phenylethyl]urea: The title urea was obtained from 1-(4-methyl-phenyl)-2-phenyl-ethylamine (3.00 g, crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.24 (s, 3 H) 2.89 (d, J=7.62 Hz, 2 H) 3.15 (q, J=5.18 Hz, 1 H) 3.24 (q, J=5.28 Hz, 1 H) 4.21 (t, J=4.98 Hz, 1H) 4.37 (t, J=5.13 Hz, 1 H) 4.75-4.88 (m, 1 H) 6.02 (t, J=5.72 Hz, 1 H) 6.43 (d, J=8.50 Hz, 1 H) 7.05-7.15 (m, 7 H) 7.18-7.23 (m, 2 H).

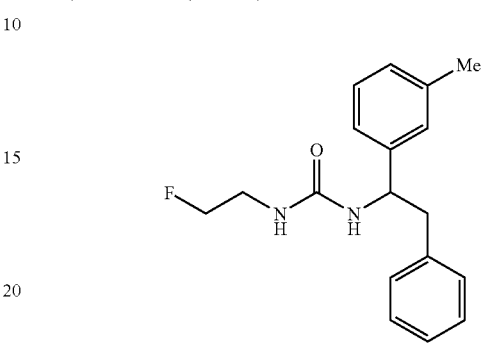

Synthesis of 1-(2-fluoroethyl)-3-[1-(3-methylphenyl)-2-phenylethyl]urea

The title compound was generated from commercially available 3-methyl-benzoyl chloride according to the general procedure B described above. The intermediates 3-methyl-N-methoxy-N-methyl-benzamide, 1-(3-methyl-phenyl)-2-phenyl-ethanone and 1-(3-methyl-phenyl)-2-phenyl-ethylamine were isolated and characterized.

3-Methyl-N-methoxy-N-methyl-benzamide[26]: The title amide was obtained from 3-methyl-benzoyl chloride (5.00 g, 32.34 mmol), N,O-dimethyl-hydroxylamine (3.50 g, 35.88 mmol), Et$_3$N (16.00 mL, 114.79 mmol) and catalytic amount of DMAP according to the protocols as outlined in general procedure B.

[26] Ottosen, Erik Rytter; Soerensen, Morten Dahl; Bjoerkling, Fredrik; Skak-Nielsen, Tine; Fjording, Marianne Scheel; Aaes, Helle; Binderup, Lise *J. Med. Chem.* 2003, 46, 5651-5662.

1-(3-Methyl-phenyl)-2-phenyl-ethanone[27]: The title ketone was obtained from 3-methyl-N-methoxy-N-methyl-benzamide (32.34 mmol, crude) and benzylmagnesium chloride (2.0 M in THF, 18.00 mL, 36.00 mmol) according to the protocols as outlined in general procedure B described above. Spectroscopic data: $^1$H NMR (300 MHz, DMSO-d$_6$) δ ppm 2.36 (s, 3 H) 4.37 (s, 2 H) 7.20-7.35 (m, 7 H) 7.41-7.48 (m, 1 H) 7.86 (s, 1 H).

[27] Otter; Shriner *J. Am. Chem. Soc.* 1951, 73, 887-888.

1-(3-Methyl-phenyl)-2-phenyl-ethylamine[28]: The title amine was obtained from 1-(3-methyl-phenyl)-2-phenyl-ethanone (32.34 mmol, crude), methoxylamine hydrochloride (4.00 g, 47.89 mmol) and BH$_3$.THF (1.0 M in THF, 60.00 mL, 60.00 mmol) according to the general procedure B described above. Spectroscopic data: $^1$H NMR (300 MHz, DMSO-d$_6$) δ ppm 2.25 (1, 3 H) 2.72-2.85 (m, 2 H) 3.94-4.00 (m, 1 H) 7.07-7.17 (m, 8 H) 7.19-7.25 (m, 1 H).

[28] Dainippon Pharm.; BE 845638 1977; *Chem.Abstr.* 88, 22977.

1-(2-Fluoroethyl)-3-[1-(3-methylphenyl)-2-phenylethyl]urea: The title urea was obtained from 1-(3-methyl-phenyl)-2-phenyl-ethylamine (3.00 g, crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.26 (s, 3 H) 2.82-2.97 (m, 2 H) 3.15 (q, J=5.18 Hz, 1 H) 3.24 (q, J=5.28 Hz, 1 H) 4.21 (t, J=5.13 Hz, 1 H) 4.37 (t, J=4.98 Hz, 1 H) 4.77-4.92 (m, 1 H) 6.02 (t, J=5.86 Hz, 1 H) 6.45 (d, J=8.50 Hz, 1 H) 6.97-7.09 (m, 3 H) 7.10-7.25 (m, 6 H).

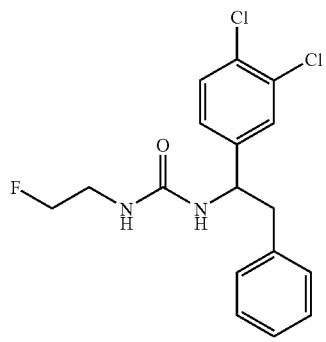

Synthesis of 1-[1-(3,4-dichlorophenyl)-2-phenyl-ethyl]-3-(2-fluoroethyl)urea

The title compound was generated from commercially available 3,4-dichloro-benzoyl chloride according to the general procedure B described above. The intermediates 1-(3,4-dichloro-phenyl)-2-phenyl-ethanone and 1-(3,4-dichloro-phenyl)-2-phenyl-ethylamine were isolated and characterized.

1-(3,4-Dichloro-phenyl)-2-phenyl-ethanone: The title ketone was obtained from 3,4-dichloro-benzoyl chloride (5.00 g, 23.87 mmol), N,O-dimethyl-hydroxylamine (3.50 g, 35.88 mmol), Et$_3$N (16.00 mL, 0.11 mol), catalytic amount of DMAP and benzylmagnesium chloride (2.0 M in THF, 14.30 mL, 28.60 mmol) according to the protocols as outlined in general procedure B described above.

1-(3,4-Dichloro-phenyl)-2-phenyl-ethylamine: The title amine was obtained from 1-(3,4-dichloro-phenyl)-2-phenyl-ethanone (23.87 mmol, crude), methoxylamine hydrochloride (4.00 g, 47.89 mmol) and BH$_3$.THF (1.0 M in THF, 60.00 mL, 60.00 mmol) according to the general procedure B described above. Spectroscopic data: $^1$H NMR (300 MHz, DMSO-d$_6$) δ ppm 2.77 (dd, J=13.34, 8.65 Hz, 1 H) 2.87-2.98 (m, 1 H) 4.17 (dd, J=8.65, 5.13 Hz, 1 H) 7.12-7.18 (m, 3 H) 7.20-7.33 (m, 4 H) 7.35-7.39 (m, 1 H).

1-[1-(3,4-Dichlorophenyl)-2-phenylethyl]-3-(2-fluoroethyl)urea: The title urea was obtained from 1-(3-methyl-phenyl)-2-phenyl-ethylamine (3.00 g, crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.86-2.96 (m, 2 H) 3.07-3.17 (m, 1 H) 3.20-3.30 (m, 1 H) 4.21 (t, J=4.98 Hz, 1 H) 4.33-4.43 (m, 1 H) 4.81-4.96 (m, 1 H) 6.11 (t, J=5.72 Hz, 1 H) 6.57 (d, J=8.21 Hz, 1 H) 6.99 (s, 1 H) 7.14-7.29 (m, 4 H) 7.48-7.63 (m, 3 H).

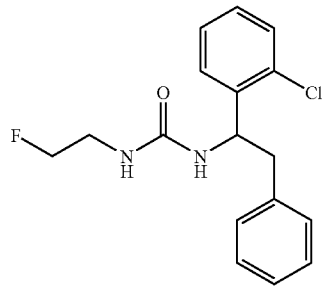

Synthesis of 1-[1-(2-chlorophenyl)-2-phenylethyl]-3-(2-fluoroethyl)urea

The title compound was generated from commercially available 2-chloro-benzoyl chloride according to the general procedure B described above. The intermediates 1-(2-chlorophenyl)-2-phenyl-ethanone and 1-(2-chloro-phenyl)-2-phenyl-ethylamine were isolated and characterized.

1-(2-Chloro-phenyl)-2-phenyl-ethanone[29]: The title ketone was obtained from 2-chloro-benzoyl chloride (5.00 g, 28.57 mmol), N,O-dimethyl-hydroxylamine (3.50 g, 35.88 mmol), Et$_3$N (16.00 mL, 0.11 mol), catalytic amount of DMAP and benzylmagnesium chloride (2.0 M in THF, 14.30 mL, 28.60 mmol) according to the protocols as outlined in general procedure B described above. Spectroscopic data: $^1$H NMR (300 MHz, DMSO-d$_6$) δ ppm 4.26 (s, 2 H) 7.22-7.32 (m, 6 H) 7.34-7.40 (m, 33 H).

[29] Jenkins; Richardson *J. Am. Chem. Soc.* 1933, 55, 1618-1619.

1-(2-Chloro-phenyl)-2-phenyl-ethylamine: The title amine was obtained from 1-(2-chloro-phenyl)-2-phenyl-ethanone (3.42 g, 14.83 mmol), methoxylamine hydrochloride (2.50 g, 29.93 mmol) and BH$_3$.THF (1.0 M in THF, 50.00 mL, 50.00 mmol) according to the general procedure B described above. Spectroscopic data: $^1$H NMR (300 MHz, DMSO-d$_6$) δ ppm 2.65 (dd, J=13.49, 9.38 Hz, 1 H) 3.14 (dd, J=13.49, 3.81 Hz, 1 H) 4.65 (dd, J=9.38, 3.81 Hz, 1 H) 7.18-7.31 (m, 8 H) 7.56 (dd, J=7.62, 1.76 Hz, 1H).

1-[1-(2-Chlorophenyl)-2-phenylethyl]-3-(2-fluoroethyl) urea: The title urea was obtained from 1-(3-methyl-phenyl)-2-phenyl-ethylamine (taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.68-2.83 (m, 1H) 2.93 (dd, J=13.78, 4.40 Hz, 1 H) 3.14 (q, J=5.28 Hz, 1 H) 3.19-3.28 (m, 1 H) 4.20 (t, J=4.98 Hz, 1 H) 4.36 (t, J=5.13 Hz, 1 H) 5.23 (dt, J=12.97, 4.65 Hz, 1 H) 6.11 (t, J=5.72 Hz, 1 H) 6.66 (d, J=8.50 Hz, 1 H) 7.15-7.31 (m, 6 H) 7.31-7.46 (m, 3 H).

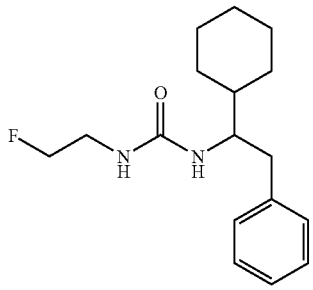

Synthesis of 1-(1-cyclohexyl-2-phenylethyl)-3-(2-fluoroethyl)urea

The title compound was generated from commercially available cyclohexanecarbonyl chloride according to the general procedure B described above. The intermediates 1-cyclohexyl-2-phenyl-ethanone and 1-cyclohexyl-2-phenyl-ethylamine were isolated and characterized.

1-Cyclohexyl-2-phenyl-ethanone[30]: The title ketone was obtained from cyclohexanecarbonyl chloride (5.00 g, 34.10 mmol), N,O-dimethyl-hydroxylamine (5.00 g, 51.26 mmol), $Et_3N$ (16.00 mL, 0.11 mol), catalytic amount of DMAP and benzylmagnesium chloride (2.0 M in THF, 20.50 mL, 41.00 mmol) according to the protocols as outlined in general procedure B described above. Spectroscopic data: $^1$H NMR (300 MHz, DMSO-$d_6$) δ ppm 1.19-1.31 (m, 3 H) 1.56-1.71 (m, 2 H) 1.72-1.88 (m, 5 H) 3.63-3.78 (m, 3 H) 7.18 (d, J=7.62 Hz, 2 H) 7.23-7.38 (m, 3 H).

[30] Inaba, Shin-ichi; Rieke, Reuben D. *J. Org. Chem.* 1985, 50, 1373-1381.

1-Cyclohexyl-2-phenyl-ethylamine[31]: The title amine was obtained from 1-cyclohexyl-2-phenyl-ethanone (crude, taken from the previous reaction), methoxylamine hydrochloride (5.00 g, 59.87 mmol) and $BH_3$.THF (1.0 M in THF, 80.00 mL, 80.00 mmol) according to the general procedure B described above. Spectroscopic data: $^1$H NMR (300 MHz, DMSO-$d_6$) δ ppm 1.14-1.30 (m, 6 H) 1.74-1.85 (m, 4 H) 2.33-2.46 (m, 1 H) 2.77-2.92 (m, 2 H) 7.17-7.33 (m, 5 H).

[31] Ghosh, P. et al. *Arzneim. Forsch.* 1978, 28, 1561-1564.

1-(1-Cyclohexyl-2-phenylethyl)-3-(2-fluoroethyl)urea: The title urea was obtained from 1-cyclohexyl-2-phenyl-ethylamine (taken from the previous step without further purification), diimidazole carbonyl (1.80 g, 11.09 mmol), fluoroethyl amine hydrochloride (1.20 g, 90% purity, 10.85 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 1.01-1.14 (m, 4 H) 1.24 (m, 1 H) 1.70 (m, 4H) 2.49 (m, 2 H) 2.53 (d, J=8.80 Hz, 1 H) 2.70 (dd, J=13.78, 5.57 Hz, 1 H) 3.08-3.20 (m, 1 H) 3.21-3.28 (m, 1 H) 3.65 (ddd, J=13.85, 8.87, 5.42 Hz, 1 H) 4.20 (td, J=9.60, 4.25 Hz, 1 H) 4.36 (td, J=9.53, 4.40 Hz, 1 H) 5.80(d, J=9.09 Hz, 1 H) 5.88(t, J=5.72 Hz, 1 H) 7.11-7.26(m, 5 H).

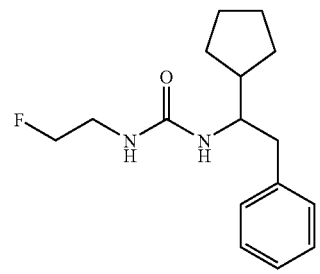

Synthesis of 1-(1-cyclopentyl-2-phenylethyl)-3-(2-fluoroethyl)urea

The title compound was generated from commercially available cyclopentanecarbonyl chloride according to the general procedure B described above. The intermediates 1-(2-chloro-phenyl)-2-phenyl-ethanone and 1-(2-chloro-phenyl)-2-phenyl-ethylamine were isolated and characterized.

1-Cyclopentyl-2-phenyl-ethanone[32]: The title ketone was obtained from cyclopentanecarbonyl chloride (4.60 g, 34.69 mmol), N,O-dimethyl-hydroxylamine (5.40 g, 55.36 mmol), $Et_3N$ (20.00 mL, 0.14 mol), catalytic amount of DMAP and benzylmagnesium chloride (2.0 M in THF, 21.00 mL, 42.00 mmol) according to the protocols as outlined in general procedure B described above. Spectroscopic data: $^1$H NMR (300 MHz, DMSO-$d_6$) δ ppm 1.52-1.87 (m, 8 H) 3.69-3.74 (m, 3 H) 7.16-7.37 (m, 5 H).

[32] Selikson; Watt *J. Org. Chem.* 1975, 40, 267.

1-Cyclopentyl-2-phenyl-ethylamine: The title amine was obtained from 1-cyclopentyl-2-phenyl-ethanone (crude, taken from the previous reaction), methoxylamine hydrochloride (5.00 g, 59.87 mmol) and $BH_3$.THF (1.0 M in THF, 80.00 mL, 80.00 mmol) according to the general procedure B described above. Spectroscopic data: $^1$H NMR (300 MHz, DMSO-$d_6$) δ ppm 1.21-1.36 (m, 2 H) 1.52-1.68 (m, 4 H) 1.73-1.87 (m, 2 H) 2.34-2.51 (m, 2 H) 2.80-2.96 (m, 2 H) 7.18-7.33 (m, 5 H).

1-(1-Cyclopentyl-2-phenylethyl)-3-(2-fluoroethyl)urea: The title urea was obtained from 1-cyclopentyl-2-phenyl-ethylamine (3.00 g, crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 1.24 (m, 2 H) 1.34-1.47 (m, 2 H) 1.47-1.63 (m, 4 H) 1.77 (m, 1 H) 2.51-2.61 (m, 1 H) 2.64-2.75 (m, 1 H) 3.16 (q, J=5.47 Hz, 1 H) 3.22-3.29 (m, 1 H) 3.73 (dt, J=14.44, 7.29 Hz, 1 H) 4.14-4.28 (m, 1 H) 4.37 (ddd, J=9.60, 7.55, 4.25 Hz, 1 H) 5.80 (d, J=9.09 Hz, 1 H) 5.90 (t, J=5.72 Hz, 1 H) 7.06-7.19 (m, 3 H) 7.19-7.33 (m, 2 H).

29

General Procedure C for the Synthesis of Fluoroethyl Substituted 1,2-diarylethyl Ureas:

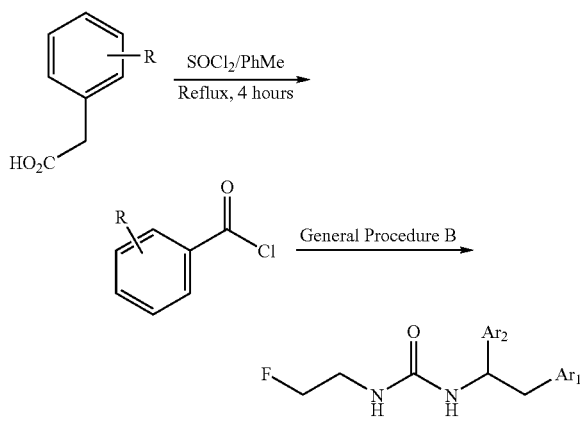

Thionyl chloride (2-4 eq) and a substituted phenylacetic acid was mixed in toluene and refluxed for 4 hours. Concentration gave the crude acid chloride, which was converted to the desired title fluoroethyl urea using the protocol described in general procedure B described above.

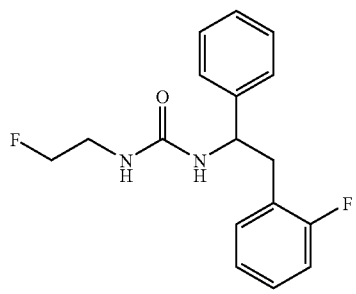

Synthesis of 1-(2-fluoroethyl)-3-[2-(2-fluorophenyl)-1-phenylethyl]urea

The title compound was generated from commercially available (2-fluorophenyl)acetic acid according to the general procedure C described above. The intermediates 2-(2-fluorophenyl)-1-phenyl-ethanone and 2-(2-fluoro-phenyl)-1-phenyl-ethylamine were isolated and characterized.

2-(2-Floro-phenyl)-1-phenyl-ethanone[33]: The title ketone was obtained from (2-fluorophenyl)acetic acid (10.00 g, 64.88 mmol), thionyl chloride (10.00 mL, 137.09 mmol), N,O-dimethyl-hydroxylamine (5.00 g, 51.26 mmol), $Et_3N$ (20.00 mL, 0.14 mol), catalytic amount of DMAP and phenylmagnesium chloride (2.0 M in THF, 12.00 mL, 24.00 mmol) according to the protocols as outlined in general procedure C described above. Spectroscopic data: $^1H$ NMR (300 MHz, DMSO-$d_6$) δ ppm 4.46 (s, 2 H) 7.11-7.19 (m, 3 H) 7.25-7.35 (m, 3 H) 7.54 (t, J=7.77 Hz, 1 H) 7.62-7.68 (m, 1 H) 8.02-8.09 (m, 1 H).

[33] Sternbach et al. *J. Org. Chem.* 1962, 27, 3781-3786.

2-(2-Fluoro-phenyl)-1-phenyl-ethylamine: The title amine was obtained from 2-(2-fluorophenyl)-1-phenyl-ethanone (crude, taken from the previous reaction), methoxylamine hydrochloride (3.00 g, 35.92 mmol) and $BH_3$.THF (1.0 M in THF, 60.00 mL, 60.00 mmol) according to the general procedure C described above.

30

1-(2-Fluoroethyl)-3-[2-(2-fluorophenyl)-1-phenylethyl] urea: The title urea was obtained from 2-(2-fluorophenyl)-1-phenyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1H$ NMR (300 MHz, DMSO-$d_6$) δ ppm 2.94 (d, J=6.16 Hz, 2 H) 3.07-3.19 (m, 1 H) 3.20-3.33 (m, 1 H) 4.20 (t, J=4.98 Hz, 1 H) 4.36 (t, J=5.13 Hz, 1 H) 4.86-5.00 (m, 1 H) 6.07 (t, J=5.57 Hz, 1 H) 6.57 (d, J=8.80 Hz, 1 H) 6.99-7.13 (m, 2 H) 7.16-7.31 (m, 7 H).

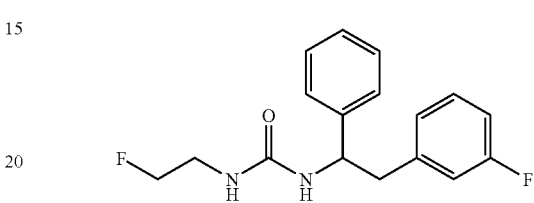

Synthesis of N-(2-fluoroethyl)-N'-[2-(3-fluorophenyl)-1-phenylethyl]urea

The title compound was generated from commercially available (3-fluorophenyl)acetic acid according to the general procedure C described above. The intermediates 2-(3-fluorophenyl)-1-phenyl-ethanone and 2-(3-fluoro-phenyl)-1-phenyl-ethylamine were isolated and characterized.

2-(3-Floro-phenyl)-1-phenyl-ethanone[34]: The title ketone was obtained from (3-fluorophenyl)acetic acid (5.00 g, 32.44 mmol), thionyl chloride (5.00 mL, 68.55 mmol), N,O-dimethyl-hydroxylamine (5.00 g, 51.26 mmol), $Et_3N$ (20.00 mL, 0.14 mol), catalytic amount of DMAP and phenylmagnesium chloride (2.0 M in THF, 18.00 mL, 36.00 mmol) according to the protocols as outlined in general procedure C described above. Spectroscopic data: $^1H$ NMR (300 MHz, DMSO-$d_6$) δ ppm 4.43 (s, 2 H) 7.01-7.16 (m, 3 H) 7.27-7.39 (m, 2 H) 7.40-7.49 (m, 1 H) 7.49-7.58 (m, 1 H) 7.59-7.70 (m, 1 H) 8.03 (dd, J=8.35, 1.32 Hz, 1 H).

[34] Fischer et al. *J. Chem. Soc.* 1962, 3318-3319.

2-(3-Fluoro-phenyl)-1-phenyl-ethylamine: The title amine was obtained from 2-(3-fluorophenyl)-1-phenyl-ethanone (crude, taken from the previous reaction), methoxylamine hydrochloride (3.00 g, 35.92 mmol) and $BH_3$.THF (1.0 M in THF, 50.00 mL, 50.00 mmol) according to the general procedure C described above. Spectroscopic data: $^1H$ NMR (300 MHz, DMSO-$d_6$) δ ppm 2.73-2.89 (m, 2 H) 4.03 (br s, 1 H) 6.91-7.06 (m, 4 H) 7.18-7.35 (m, 4 H) 7.56-7.71 (m, 1 H).

1-(2-Fluoroethyl)-3-[2-(3-fluorophenyl)-1-phenylethyl] urea: The title urea was obtained from 2-(3-fluorophenyl)-1-phenyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1H$ NMR (300 MHz, DMSO-$d_6$) δ ppm 2.87-3.00 (m, 2 H) 3.16 (q, J=5.08 Hz, 1 H) 3.25 (q, J=5.28 Hz, 1 H) 4.21 (t, J=5.13 Hz, 1 H) 4.37 (t, J=4.98 Hz, 1 H) 4.81-4.95 (m, 1 H) 6.05 (t, J=5.72 Hz, 1 H) 6.52 (d, J=8.80 Hz, 1 H) 6.91-7.01 (m, 3 H) 7.16-7.32 (m, 6 H).

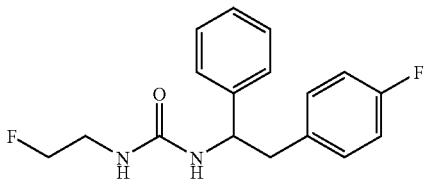

Synthesis of 1-(2-fluoroethyl)-3-[2-(4-fluorophenyl)-1-phenylethyl]urea

The title compound was generated from commercially available (4-fluorophenyl)acetic acid according to the general procedure C described above. The intermediates 2-(4-fluoro-phenyl)-1-phenyl-ethanone and 2-(4-fluoro-phenyl)-1-phenyl-ethylamine were isolated and characterized.

2-(4-Floro-phenyl)-1-phenyl-ethanone[35]: The title ketone was obtained from (4-fluorophenyl)acetic acid (5.00 g, 32.44 mmol), thionyl chloride (5.00 mL, 68.55 mmol), N,O-dimethyl-hydroxylamine (5.00 g, 51.26 mmol), Et$_3$N (20.00 mL, 0.14 mol), catalytic amount of DMAP and phenylmagnesium chloride (2.0 M in THF, 18.00 mL, 36.00 mmol) according to the protocols as outlined in general procedure C described above. Spectroscopic data: $^1$H NMR (300 MHz, DMSO-d$_6$) δ ppm 4.39 (s, 2 H) 7.08-7.17 (m, 2 H) 7.19-7.31 (m, 3 H) 7.58-7.74 (m, 2 H) 8.03 (d, J=8.21 Hz, 2 H).

2-(4-Fluoro-phenyl)-1-phenyl-ethylamine[35]: The title amine was obtained from 2-(4-fluorophenyl)-1-phenyl-ethanone (crude, taken from the previous reaction), methoxylamine hydrochloride (4.00 g, 47.89 mmol) and BH$_3$.THF (1.0 M in THF, 50.00 mL, 50.00 mmol) according to the general procedure C described above.

[35] Gee, Kyle R.; Barmettler, Peter; Rhodes, Michael R.; McBurney, Robert N.; Reddy, N. Laxma; et al. *J. Med. Chem.* 1993, 36, 1938-1946.

1-(2-Fluoroethyl)-3-[2-(4-fluorophenyl)-1-phenylethyl]urea: The title urea was obtained from 2-(4-fluorophenyl)-1-phenyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.81-2.96 (m, 2H) 3.16 (q, J=5.47 Hz, 1 H) 3.25 (q, J=5.37 Hz, 1 H) 4.21 (t, J=5.13 Hz, 1 H) 4.37 (t, J=5.13 Hz, 1 H) 4.75-4.89 (m, 1 H) 6.04 (t, J=5.72 Hz, 1 H) 6.49 (d, J=8.50 Hz, 1 H) 6.94-7.08 (m, 2 H) 7.11-7.19 (m, 3 H) 7.21-7.28 (m, 4 H).

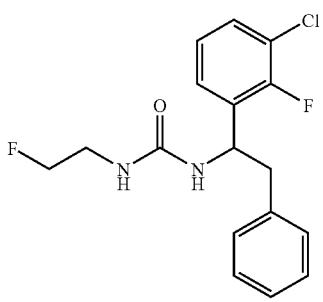

Synthesis of 1-[1-(3-chloro-2-fluorophenyl)-2-phenylethyl]-3-(2-fluoroethyl)urea The title compound was generated from commercially available 3-chloro-2-fluoro-benzoic acid according to the general procedure C described above. The intermediates 1-(3-chloro-2-fluoro-phenyl)-2-phenyl-ethanone and 1-(3-chloro-2-fluoro-phenyl)-2-phenyl-ethylamine were isolated and characterized.

1-(3-Chloro-2-fluoro-phenyl)-2-phenyl-ethanone: The title ketone was obtained from 3-chloro-2-fluorobenzoic acid (10.00 g, 57.29 mmol), thionyl chloride (10.00 mL, 137.09 mmol), N,O-dimethyl-hydroxylamine (5.00 g, 51.26 mmol), Et$_3$N (20.00 mL, 0.14 mol), catalytic amount of DMAP and benzylmagnesium chloride (2.0 M in THF, 20.00 mL, 40.00 mmol) according to the protocols as outlined in general procedure C described above. Spectroscopic data: $^1$H NMR (300 MHz, DMSO-d$_6$) 4.33 (d, J=1.76 Hz, 2 H) 7.19-7.35 (m, 6 H) 7.82 (t, J=7.33 Hz, 2 H).

1-(3-Chloro-2-fluoro-phenyl)-2-phenyl-ethylamine: The title amine was obtained from 1-(3-chloro-2-fluoro-phenyl)-2-phenyl-ethanone (crude, taken from the previous reaction), methoxylamine hydrochloride (3.00 g, 35.92 mmol) and BH$_3$.THF (1.0 M in THF, 60.00 mL, 60.00 mmol) according to the general procedure C described above. Spectroscopic data: $^1$H NMR (300 MHz, DMSO-d$_6$) δ ppm 3.30-3.39 (m, 2 H) 4.29 (t, J=4.98 Hz, 1 H) 7.06-7.08 (m, 2 H) 7.16-7.25 (m, 3 H) 7.34-7.39 (m, 3 H).

1-[1-(3-chloro-2-fluorophenyl)-2-phenylethyl]-3-(2-fluoroethyl)urea: The title urea was obtained from 1-(3-chloro-2-fluoro-phenyl)-2-phenyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.84-2.99 (m, 2 H) 3.04-3.19 (m, 1 H) 3.21-3.29 (m, 1 H) 4.22 (t, J=4.98 Hz, 1 H) 4.38 (t, J=4.98 Hz, 1 H) 5.13 (q, J=7.82 Hz, 1 H) 6.16 (t, J=5.57 Hz, 1 H) 6.67 (d, J=8.21 Hz, 1 H) 7.09-7.25 (m, 8 H) 7.41 (t, J=7.48 Hz, 1 H).

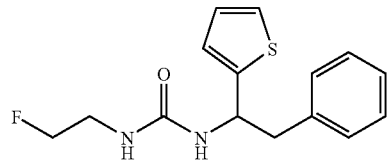

Synthesis of 1-(2-fluoroethyl)-3-[2-phenyl-1-(2-thienyl)ethyl]urea

The title compound was generated from commercially available thiophene-2-carbonyl chloride according to the general procedure B described above. The intermediates 2-phenyl-1-thiophen-2-yl-ethanone and 2-phenyl-1-thiophen-2-yl-ethylamine were isolated and characterized.

2-Phenyl-1-thiophen-2-yl-ethanone[36]: The title ketone was obtained from thiophene-2-carbonyl chloride (5.00 g, 34.11 mmol), N,O-dimethyl-hydroxylamine (4.50 g, 46.13 mmol), Et$_3$N (15.00 mL, 0.11 mol), catalytic amount of DMAP and benzylmagnesium chloride (2.0 M in THF, 16.00 mL, 32.000 mmol) according to the protocols as outlined in general procedure B described above.

[36] Ott; *Org. Synth. Isotopes* 1958, 152.

2-Phenyl-1-thiophen-2-yl-ethylamine[37]: The title amine was obtained from 2-phenyl-1-thiophen-2-yl-ethanone (crude), methoxylamine hydrochloride (4.00 g, 47.89 mmol) and $BH_3$.THF (1.0 M in THF, 60.00 mL, 60.00 mmol) according to the general procedure B described above. Spectroscopic data: $^1$H NMR (300 MHz, DMSO-$d_6$) δ ppm 2.80-2.88 (m, 1 H) 2.91-2.98 (m, 1 H) 4.34 (t, J=6.89 Hz, 1 H) 6.81-6.95 (m, 2 H) 7.16 (t, J=7.92 Hz, 3 H) 7.21-7.30 (m, 3 H).

[37] Hill; Brooks *J. Org. Chem.* 1958, 23, 1289-1290.

1-(2-Fluoroethyl)-3-[2-phenyl-1-(2-thienyl)ethyl]urea: The title urea was obtained from 2-phenyl-1-thiophen-2-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.95-3.10 (m, 2 H) 3.18 (q, J=5.18 Hz, 1 H) 3.24-3.30 (m, 1 H) 4.22 (t, J=5.13 Hz, 1 H) 4.38 (t, J=4.98 Hz, 1 H) 5.09-5.22 (m, 1 H) 6.07 (t, J=5.72 Hz, 1 H) 6.50 (d, J=8.80 Hz, 1 H) 6.88-6.97 (m, 2 H) 7.13-7.26 (m, 5 H) 7.32 (dd, J=4.54, 1.61 Hz, 1 H).

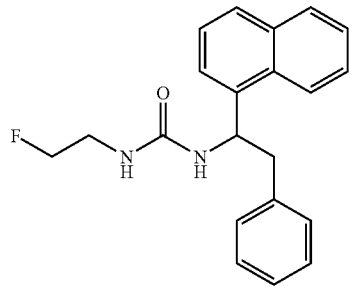

Synthesis of 1-(2-fluoroethyl)-3-[1-(1-naphthyl)-2-phenylethyl]urea

The title compound was generated from commercially available naphthalene-1-carbonyl chloride according to the general procedure B described above. The intermediates 1-naphthalen-1-yl-2-phenyl-ethanone and 1-naphthalen-1-yl-2-phenyl-ethylamine were isolated and characterized.

1-Naphthalen-1-yl-2-phenyl-ethanone[38]: The title ketone was obtained from naphthalene-1-carbonyl chloride (5.00 g, 26.23 mmol), N,O-dimethyl-hydroxylamine (5.00 g, 51.26 mmol), $Et_3N$ (16.00 mL, 0.11 mol), catalytic amount of DMAP and benzylmagnesium chloride (2.0 M in THF, 18.00 mL, 36.00 mmol) according to the protocols as outlined in general procedure B described above.

[38] Hecht, S. S. et al. *J. Med. Chem.* 1978, 21, 38-44.

1-Naphthalen-1-yl-2-phenyl-ethylamine[39]: The title amine was obtained from 1-naphthalen-1-yl-2-phenyl-ethanone (crude), methoxylamine hydrochloride (4.80 g, 57.47 mmol) and $BH_3$.THF (1.0 M in THF, 60.00 mL, 60.00 mmol) according to the general procedure B described above.

[39] Breon & Co. U.S. Pat. No. 2,711,428 1948.

1-(2-Fluoroethyl)-3-[1-(1-naphthyl)-2-phenylethyl]urea: The title urea was obtained from 1-naphthalen-1-yl-2-phenyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.86-3.01 (m, 1 H) 3.09-3.20 (m, 2 H) 3.22-3.29 (m, 1 H) 4.20 (t, J=4.84 Hz, 1 H) 4.36 (t, J=4.98 Hz, 1 H) 5.66-5.79 (m, 1 H) 6.08 (t, J=5.57 Hz, 1 H) 6.67 (d, J=8.21 Hz, 1 H) 7.05-7.19 (m, 1 H) 7.20-7.30 (m, 4 H) 7.45-7.60 (m, 4 H) 7.80 (d, J=7.62 Hz, 1 H) 7.92 (d, J=7.92 Hz, 1 H) 8.19 (d, J=8.50 Hz, 1 H).

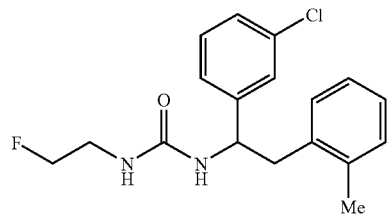

Synthesis of 1-[1-(3-chlorophenyl)-2-(2-methylphenyl)ethyl]-3-(2-fluoroethyl)urea The title compound was generated from commercially available o-tolyl-acetic acid according to the general procedure C described above. The intermediates 1-(3-chloro-phenyl)-2-o-tolyl-ethanone and 1-(3-chloro-phenyl)-2-o-tolyl-ethylamine were isolated and characterized.

1-(3-Chloro-phenyl)-2-o-tolyl-ethanone: The title ketone was obtained from o-tolyl-acetic acid (5.00 g, 33.30 mmol), thionyl chloride (5.00 mL, 68.55 mmol), N,O-dimethyl-hydroxylamine (5.00 g, 51.26 mmol), $Et_3N$ (20.00 mL, 0.14 mol), catalytic amount of DMAP and 3-chlorophenylmagnesium bromide (0.5 M in THF, 50.00 mL, 25.00 mmol) according to the protocols as outlined in general procedure C described above. Spectroscopic data: $^1$H NMR (300 MHz, DMSO-$d_6$) δ ppm 2.13 (s, 3 H) 4.45 (s, 2 H) 7.05-7.19 (m, 4 H) 7.23-7.38 (m, 1 H) 7.58 (t, J=7.92 Hz, 1 H) 7.94-8.08 (m, 2 H).

1-(3-Chloro-phenyl)-2-o-tolyl-ethylamine: The title amine was obtained from 1-(3-chloro-phenyl)-2-O— tolyl-ethanone (crude, taken from the previous reaction), methoxylamine hydrochloride (3.50 g, 41.91 mmol) and $BH_3$.THF (1.0 M in THF, 60.00 mL, 60.00 mmol) according to the general procedure C described above. Spectroscopic data: $^1$H NMR (300 MHz, DMSO-$d_6$) δ ppm 2.26 (d, J=8.16 Hz, 2 H) 4.01 (t, J=8.16 Hz, 1 H) 7.00-7.12 (m, 4 H) 7.17-7.28 (m, 3 H) 7.35 (s, 1 H).

1-[1-(3-Chlorophenyl)-2-(2-methylphenyl)ethyl]-N'(2-fluoroethyl) urea: The title urea was obtained from 1-(3-chloro-phenyl)-2-o-tolyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.20 (s, 3 H), 2.87-2.90 (m, 2 H) 3.16 (q, J=5.08 Hz, 1 H) 3.25 (q, J=5.28 Hz, 1 H) 4.22 (t, J=5.13 Hz, 1 H) 4.37 (t, J=4.98 Hz, 1 H) 4.86 (q, J=7.92 Hz, 1 H) 6.09 (t, J=5.72 Hz, 1 H) 6.60 (d, J=8.50 Hz, 1 H) 7.00-7.12 (m, 4 H) 7.16 (d, J=7.04 Hz, 1 H) 7.22-7.35 (m, 3 H).

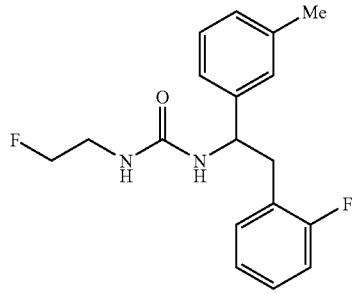

Synthesis of 1-(2-fluoro-ethyl)-3-[2-(2-fluoro-phenyl)-1-m-tolyl-ethyl]-urea

The title compound was generated from commercially available 2-fluorophenylacetic acid according to the general procedure C described above. The intermediates 2-(2-fluoro-phenyl)-1-m-tolyl-ethanone and 2-(2-fluoro-phenyl)-1-m-tolyl-ethylamine were isolated and characterized.

2-(2-Fluoro-phenyl)-1-m-tolyl-ethanone: The title ketone was obtained from 2-fluorophenylacetic acid (10.00 g, 64.88 mmol), thionyl chloride (10.00 mL, 137.09 mmol), N,O-dimethyl-hydroxylamine (8.30 g, 99.38 mmol), Et$_3$N (20.00 mL, 0.14 mol), catalytic amount of DMAP and 3-tolylmagnesium chloride (1.0 M in THF, 60.00 mL, 60.00 mmol) according to the protocols as outlined in general procedure C described above. Spectroscopic data: $^1$H NMR (300 MHz, DMSO-d$_6$) δ ppm 2.38 (s, 3 H) 4.44 (s, 2 H) 7.16 (t, J=7.33 Hz, 2 H) 7.31 (t, J=7.48 Hz, 2 H) 7.38-7.48 (m, 3 H) 7.81 (s, 1 H).

2-(2-Fluoro-phenyl)-1-m-tolyl-ethylamine: The title amine was obtained from 2-(2-fluoro-phenyl)-1-m-tolyl-ethanone (2.80 g, 12.26 mmol), methoxylamine hydrochloride (3.00 g, 35.92 mmol) and BH$_3$.THF (1.0 M in THF, 35.00 mL, 35.00 mmol) according to the general procedure C described above.

1-(2-Floro-ethyl)-3-[2-(2-fluoro-phenyl)-1-m-tolyl-ethyl]-urea: The title urea was obtained from 2-(2-fluorophenyl)-1-m-tolyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.26 (s, 3 H) 2.84-2.99 (m, 2 H) 3.14 (q, J=5.28 Hz, 1 H) 3.20-3.28 (m, 1 H) 4.13-4.24 (m, 1 H) 4.30-4.41 (m, 1 H) 4.78-4.93 (m, 1 H) 6.03 (t, J=5.86 Hz, 1 H) 6.51 (d, J=8.80 Hz, 1 H) 6.96-7.09 (m, 4 H) 7.10-7.25 (m, 4 H).

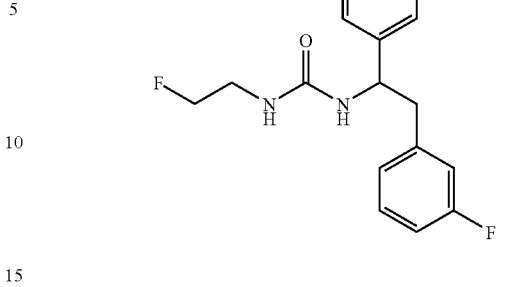

Synthesis of 1-(2-fluoroethyl)-3-[2-(3-fluorophenyl)-1-m-tolylethyl]urea

The title compound was generated from commercially available 3-fluorophenylacetic acid according to the general procedure C described above. The intermediates 2-(3-fluorophenyl)-1-m-tolyl-ethanone and 2-(3-fluoro-phenyl)-1-m-tolyl-ethylamine were isolated and characterized.

2-(3-Fluoro-phenyl)-1-m-tolyl-ethanone: The title ketone was obtained from 3-fluorophenylacetic acid (5.00 g, 32.44 mmol), thionyl chloride (5.00 mL, 68.55 mmol), N,O-dimethyl-hydroxylamine (4.70 g, 48.18 mmol), Et$_3$N (16.00 mL, 0.11 mol), catalytic amount of DMAP and m-tolylmagnesium chloride (1.0 M in THF, 80.00 mL, 80.00 mmol) according to the protocols as outlined in general procedure C described above. Spectroscopic data: $^1$H NMR (300 MHz, DMSO-d$_6$) δ ppm 2.37 (s, 3 H) 4.41 (s, 2 H) 7.01-7.15 (m, 4 H) 7.38-7.47 (m, 3 H) 7.85 (s, 1 H).

2-(3-Fluoro-phenyl)-1-m-tolyl-ethylamine: The title amine was obtained from 2-(3-fluorophenyl)-1-m-tolyl-ethanone (1.30 g, 5.70 mmol), methoxylamine hydrochloride (1.50 g, 17.96 mmol) and BH$_3$.THF (1.0 M in THF, 20.00 mL, 20.00 mmol) according to the general procedure C described above. Spectroscopic data: $^1$H NMR (300 MHz, DMSO-d$_6$) δ ppm 2.25 (s, 3 H) 2.73-2.87 (m, 2 H) 3.97 (br s, 6H) 6.86-7.00 (m, 4 H) 7.04-7.18 (m, 3 H) 7.20-7.29 (m, 1 H).

1-(2-Fluoroethyl)-3-[2-(3-fluorophenyl)-1-m-tolylethyl] urea: The title urea was obtained from 2-(3-fluorophenyl)-1-phenyl-ethylamine (crude, taken from the previous step without further purification), diimidazole carbonyl (0.82 g, 5.00 mmol), fluoroethyl amine hydrochloride (0.50 g, 90% purity, 4.52 mmol) and diisopropylethyl amine (2.00 mL, 11.48 mmol) according to the protocols as outlined in general procedure A above. Spectroscopic data: $^1$H NMR (300 MHz, DMSO-d$_6$) δ ppm 2.27 (s, 3 H) 2.84-2.99 (m, 2 H) 3.07-3.19 (m, 1 H) 3.20-3.29 (m, 1 H) 4.20 (t, J=4.98 Hz, 1 H) 4.36 (t, J=4.98 Hz, 1 H) 4.76-4.90 (m, 1 H) 5.94-6.09 (m, 1 H) 6.47 (d, J=8.80 Hz, 1 H) 6.94-7.09 (m, 5 H) 7.14-7.29 (m, 3H).

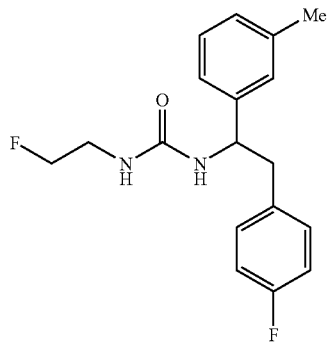

Synthesis of 1-(2-fluoroethyl)-3-[2-(4-fluorophenyl)-1-m-tolylethyl]urea

The title compound was generated from commercially available 4-fluorophenylacetic acid according to the general procedure C described above. The intermediates 2-(4-fluoro-phenyl)-1-m-tolyl-ethanone and 2-(4-fluoro-phenyl)-1-m-tolyl-ethylamine were isolated and characterized.

2-(4-Fluoro-phenyl)-1-m-tolyl-ethanone[40]: The title ketone was obtained from 4-fluorophenylacetic acid (5.00 g, 32.44 mmol), thionyl chloride (5.00 mL, 68.55 mmol), N,O-dimethyl-hydroxylamine (4.70 g, 48.18 mmol), Et$_3$N (20.00 mL, 0.14 mol), catalytic amount of DMAP and m-tolylmagnesium chloride (1.0 M in THF, 18.00 mL, 36.00 mmol) according to the protocols as outlined in general procedure C described above. Spectroscopic data: $^1$H NMR (300 MHz, DMSO-d$_6$) δ ppm 2.28 (s, 3 H) 4.37 (s, 2 H) 7.06-7.17 (m, 3 H) 7.20-7.32 (m, 2 H) 7.37-7.46 (m, 2 H) 7.84 (s, 1 H).

[40] Moffett, R. B.; Hester, J. B. *J. Med. Chem.* 1972, 15, 1243-1247.

2-(4-Fluoro-phenyl)-1-m-tolyl-ethylamine: The title amine was obtained from 2-(4-fluorophenyl)-1-m-tolyl-ethanone (crude, taken from the previous reaction), methoxylamine hydrochloride (3.00 g, 35.92 mmol) and BH$_3$.THF (1.0 M in THF, 35.00 mL, 35.00 mmol) according to the general procedure C described above.

1-(2-Fluoroethyl)-3-[2-(4-fluorophenyl)-1-m-tolylethyl] urea: The title urea was obtained from 2-(4-fluorophenyl)-1-m-tolyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.26 (s, 3 H) 2.81-2.95 (m, 2 H) 3.09-3.20 (m, 1 H) 3.25 (q, J=4.98 Hz, 1 H) 4.21 (t, J=4.84 Hz, 1 H) 4.37 (t, J=4.84 Hz, 1 H) 4.81 (q, J=7.92 Hz, 1 H) 6.02 (t, J=5.57 Hz, 1 H) 6.46 (d, J=8.50 Hz, 1 H) 6.97-7.09 (m, 5 H) 7.10-7.22 (m, 3 H).

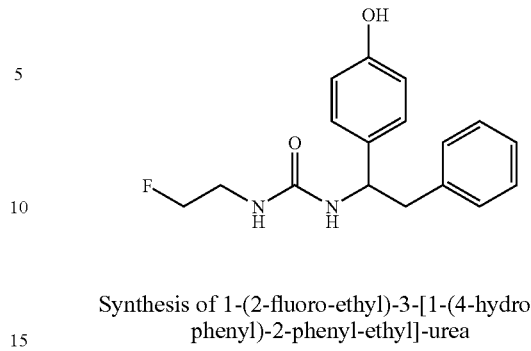

Synthesis of 1-(2-fluoro-ethyl)-3-[1-(4-hydroxy-phenyl)-2-phenyl-ethyl]-urea The desired amine was generated from the commercially available 1-(4-hydroxy-phenyl)-2-phenyl-ethanone using chemistry described in the following scheme. The title compound was thus generated from this amine according to the protocols described in general procedure A. The intermediates 1-(4-hydroxy-phenyl)-2-phenyl-ethanone O-methyl-oxime and 4-(1-amino-2-phenyl-ethyl)-phenol were separated and characterized.

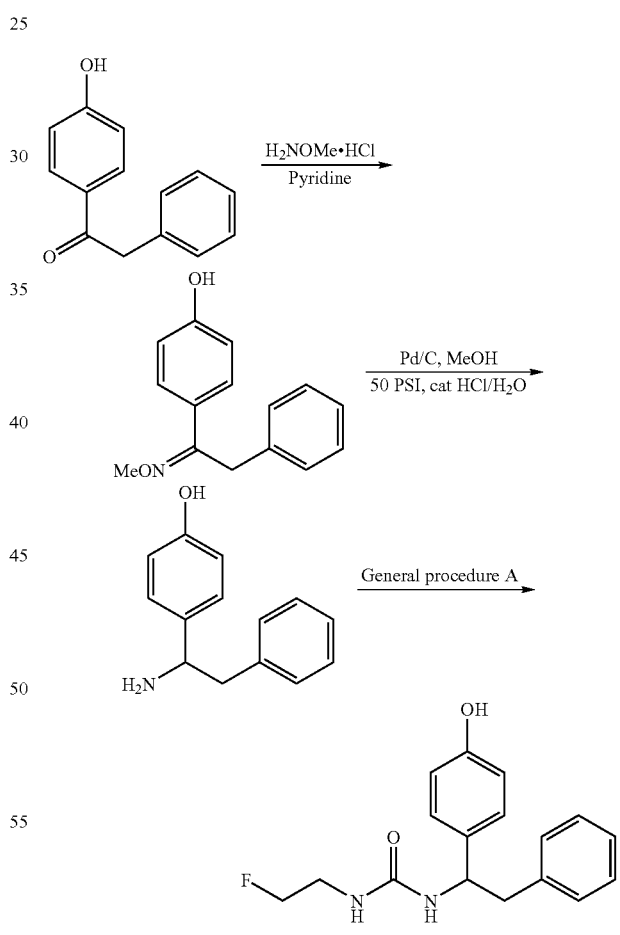

1-(4-Hydroxy-phenyl)-2-phenyl-ethanone O-methyl-oxime: 1-(4-hydroxy-phenyl)-2-phenyl-ethanone (10.00 g, 47.12 mmol) was dissolved in pyridine (60 mL) and methoxylamine hydrochloride (5.90 g, 70.64 mmol) was added. The resulting reaction mixture was stirred at room temperature for 14 hours, and then concentrated. The solids were washed with ether, and the ether layers were combined and concentrated to afford the desired title compound. Spectroscopic data: $^1$H NMR (300 MHz, DMSO-$d_6$) δ ppm 3.90 (s, 3 H) 4.06 (s, 2 H) 6.73 (d, J=8.21 Hz, 1 H) 7.18 (dt, J=15.46, 7.66 Hz, 2 H) 7.38-7.44 (m, 1H) 7.50 (d, J=7.92 Hz, 1 H) 7.81 (s, 2 H) 8.55-8.64 (m, 2 H).

4-(1-Amino-2-phenyl-ethyl)-phenol[41]: 1-(4-Hydroxy-phenyl)-2-phenyl-ethanone O-methyl-oxime (crude, taken from the previous step without further purification) was dissolved in methanol (80 mL), and then Pd/C (1.00 g) was added, followed by the addition of a couple of drops of concentrated HCl and a couple of drops of water. The resulting mixture was hydrogenated under 50 psi of hydrogen for 14 hours. Filtration and followed concentration afforded the crude title compound. Spectroscopic data: $^1$H NMR (300 MHz, DMSO-$d_6$) δ ppm 2.73-2.76 (m, 2 H) 3.94 (t, J=6.89 Hz, 1 H) 6.51-6.66 (m, 2 H) 7.06-7.15 (m, 5 H) 7.17-7.23 (m, 2 H).
[41] Dankowa et al. *Zh. Obshch. Khim.* 1951, 21, 787-795; engl. pages 867-875.

1-(2-Fluoro-ethyl)-3-[1-(4-hydroxy-phenyl)-2-phenyl-ethyl]urea: The title compound was obtained from 4-(1-amino-2-phenyl-ethyl)-phenol (3.00 g, 14.08 mmol),), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) 6 pp 2.89 (d, J=7.33 Hz, 2 H) 4.23 (t, J=4.98 Hz, 1 H) 4.31 (t, J=5.28 Hz, 1 H) 4.39 (t, J=4.98 Hz, 1 H) 4.47 (t, J=5.28 Hz, 1 H), 4.74-4.81 (m, 1 H) 6.02 (t, J=5.57 Hz, 1H), 6.38 (d, J=8.50 Hz, 1 H) 6.61-6.72 (m, 4 H), 7.02-7.26 (m, 5 H).

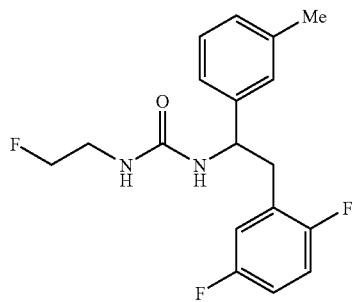

Synthesis of 1-[2-(2,5-difluoro-phenyl)-1-m-tolyl-ethyl]-3-(2-fluoro-ethyl)-urea The title compound was generated from commercially available 2,5-difluorophenylacetic acid according to the general procedure C described above. The intermediates 2-(2,5-difluoro-phenyl)-1-m-tolyl-ethanone and 2-(2,5-difluoro-phenyl)-1-m-tolyl-ethylamine were isolated and characterized.

2-(2,5-Difluoro-phenyl)-1-m-tolyl-ethanone: The title ketone was obtained from 2,5-difluorophenylacetic acid (10.00 g, 58.10 mmol), thionyl chloride (8.50 mL, 116.53 mmol), N,O-dimethyl-hydroxylamine (8.50 g, 87.14 mmol), Et$_3$N (16.00 mL, 0.11 mol), catalytic amount of DMAP and m-tolylmagnesium chloride (1.0 M in THF, 75.00 mL, 75.00 mmol) according to the protocols as outlined in general procedure C described above. Spectroscopic data: $^1$H NMR (300 MHz, DMSO-$d_6$) δ ppm 2.41 (s, 3 H) 4.49 (s, 2 H) 7.14-7.28 (m, 3 H) 7.34 (t, J=7.48 Hz, 1 H) 7.41-7.47 (m, 1 H) 7.49 (d, J=3.52 Hz, 1 H) 7.83-7.91 (m, 1 H).

2-(2,5-Difluoro-phenyl)-1-m-tolyl-ethylamine: The title amine was obtained from 2-(2,5-difluorophenyl)-1-m-tolyl-ethanone (crude, taken from the previous reaction), methoxylamine hydrochloride (3.20 g, 38.31 mmol) and BH$_3$.THF (1.0 M in THF, 100.00 mL, 0.10 mol) according to the general procedure C described above. Spectroscopic data: $^1$H NMR (300 MHz, DMSO-$d_6$) δ ppm 2.27 (s, 3 H) 2.83 (d, J=7.04 Hz, 2 H) 3.96-4.03 (m, 1 H) 6.99-7.11 (m, 2 H) 7.13-7.19 (m, 2 H) 7.34 (t, J=7.62 Hz, 1 H) 7.39-7.49 (m, 2 H).

1-[2-(2,5-Difluoro-phenyl)-1-m-tolyl-ethyl]-3-(2-fluoro-ethyl)-urea: The title urea was obtained from 2-(2,5-difluorophenyl)-1-m-tolyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.27 (s, 3 H) 2.84-2.99 (m, 2 H) 3.15 (q, J=5.37 Hz, 1 H) 3.19-3.28 (m, 1 H) 4.20 (td, J=5.06, 1.32 Hz, 1 H) 4.26-4.41 (m, 1 H) 4.83-4.96 (m, 1 H) 6.05 (t, J=5.72 Hz, 1 H) 6.52 (d, J=9.09 Hz, 1 H) 7.00-7.09 (m, 4 H) 7.09-7.22 (m, 3 H).

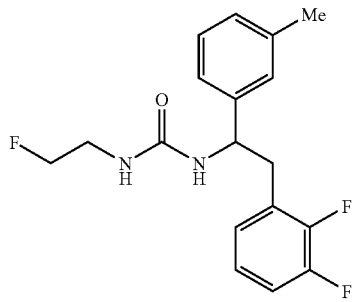

Synthesis of 1-[2-(2,3-difluoro-phenyl)-1-m-tolyl-ethyl]-3-(2-fluoro-ethyl)-urea The title compound was generated from commercially available 2,3-difluorophenylacetic acid according to the general procedure C described above. The intermediates 2-(2,3-difluoro-phenyl)-1-m-tolyl-ethanone and 2-(2,3-difluoro-phenyl)-1-m-tolyl-ethylamine were isolated and characterized.

2-(2,3-Difluoro-phenyl)-1-m-tolyl-ethanone: The title ketone was obtained from 2,3-difluorophenylacetic acid (10.00 g, 58.10 mmol), thionyl chloride (8.50 mL, 116.53 mmol), N,O-dimethyl-hydroxylamine (8.50 g, 87.14 mmol), Et$_3$N (16.00 mL, 0.11 mol), catalytic amount of DMAP and m-tolylmagnesium chloride (1.0 M in THF, 70.00 mL, 70.00 mmol) according to the protocols as outlined in general procedure C described above. Spectroscopic data: $^1$H NMR (300 MHz, DMSO-$d_6$) δ ppm 2.41 (s, 3 H) 4.56 (s, 2 H) 6.52-6.60 (m, 2 H) 6.98-7.09 (m, 1 H) 7.11-7.22 (m, 1 H) 7.28-7.41 (m, 1 H) 7.42-7.53 (m, 1 H) 7.84-7.91 (m, 1 H).

2-(2,3-Difluoro-phenyl)-1-m-tolyl-ethylamine: The title amine was obtained from 2-(2,3-difluorophenyl)-1-m-tolyl-ethanone (crude, taken from the previous reaction), methoxylamine hydrochloride (3.20 g, 38.31 mmol) and BH$_3$.THF (1.0 M in THF, 100.00 mL, 100.00 mmol) according to the general procedure C described above.

1-[2-(2,3-Difluoro-phenyl)-1-m-tolyl-ethyl]-3-(2-fluoro-ethyl)-urea: The title urea was obtained from 2-(2,3-difluorophenyl)-1-m-tolyl-ethylamine (crude, taken from the previous step without further purification), diimidazole carbonyl (0.81 g, 5.00 mmol), fluoroethyl amine hydrochloride (0.50 g, 90% purity, 4.52 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.26 (s, 3 H) 2.90-3.04 (m, 2 H) 3.09-3.19 (m, 1 H) 3.24 (q, J=5.18 Hz, 1 H) 4.20 (t, J=4.98 Hz, 1 H) 4.36 (t, J=5.13 Hz, 1 H) 4.83-4.95 (m, 1 H) 6.05 (t, J=5.72 Hz, 1 H) 6.54 (t, J=8.65 Hz, 2 H) 6.97-7.10 (m, 5 H) 7.13-7.26 (m, 2 H).

General procedure D for the Synthesis of Fluoroethyl Aryl Pyridinyl Substituted EthylUreas:

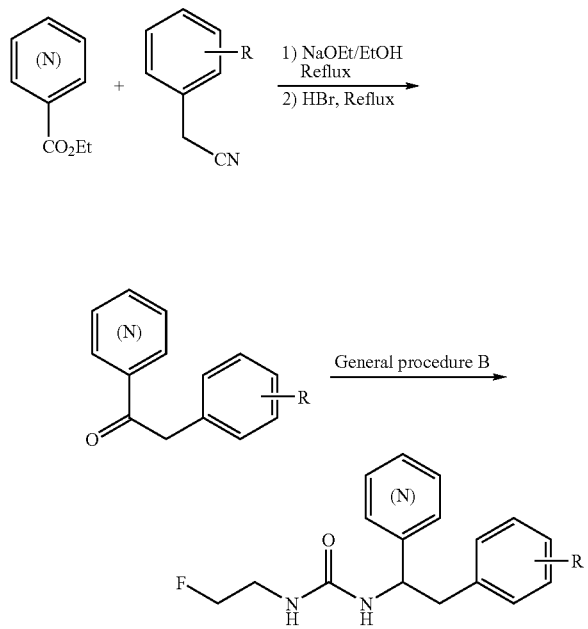

An (iso)nicotinic acid ethyl ester and a substituted phenyl acetonitrile (1:1 ratio) were dissolved in EtOH (100 mL), then sodium ethoxide (21% in EtOH, 1.0 eq was added. The resulting reaction mixture was refluxed for 3 hours, then cooled to 0° C., concentrated HCl was added to adjust the acidity to pH=3. A solid, presumably the intermediate cyanoketone, was formed and filtered. The solid was then washed with water and dried under house vacuum. This cyanoketone was mixed with 48% hydrobromic acid (80 mL) and the mixture was refluxed for 5 hours. After cooling to room temperature, the reaction mixture was basified with ammonium hydroxide, and then extracted with ethyl acetate. The combined organic phases were washed with brine, then dried with magnesium sulfate and concentrated to give the desired diaryl ketone[42]. This ketone was then converted into the desired amine via oxime intermediate according to the protocol described in general procedure B. The final fluoroethyl urea was thus obtained using this amine and fluoroethyl ammonium chloride according to general procedure A.

[42] Clader, John W.; Berger, Joel G.; Burrier, Robert E.; Davis, Harry R.; Domalski, Martin; et al. J. Med. Chem. 1995, 38, 1600-1607.

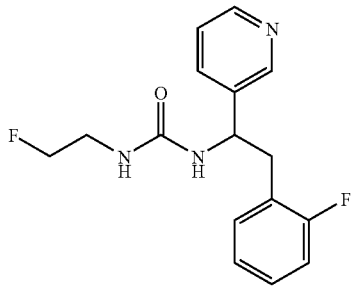

Synthesis of 1-(2-fluoro-ethyl)-3-[2-(2-fluoro-phenyl)-1-pyridin-3-yl-ethyl]-urea The title compound was generated from commercially available nicotinic acid ethyl ester and (2-fluoro-phenyl)-acetonitrile according to the general procedure D described above. The intermediates 2-(2-fluoro-phenyl)-1-pyridin-3-yl-ethanone and 2-(2-fluoro-phenyl)-1-pyridin-3-yl-ethylamine were isolated and characterized.

2-(2-Fluoro-phenyl)-1-pyridin-3-yl-ethanone: The title ketone was obtained from nicotinic acid ethyl ester (10.00 g, 66.16 mmol), (2-fluoro-phenyl)-acetonitrile (9.12 g, 67.49 mmol), sodium ethoxide (50.00 mL, 21 wt. % in EtOH, 0.13 mol) and hydrobromic acid (48%, 80.00 mL) according to the protocols as outlined in general procedure D described above. Spectroscopic data: $^1$H NMR (300 MHz, DMSO-$d_6$) δ ppm 4.53 (s, 2 H) 7.10-7.23 (m, 2 H) 7.24-7.36 (m, 2 H) 7.58 (dd, J=7.92, 5.57 Hz, 1 H) 8.36 (dt, J=8.14, 1.94 Hz, 1 H) 8.81 (dd, J=4.84, 1.61 Hz, 1 H) 9.22 (d, J=1.47 Hz, 1 H).

2-(2-Fluoro-phenyl)-1-pyridin-3-yl-ethylamine: The title amine was obtained from 2-(2-fluoro-phenyl)-1-pyridin-3-yl-ethanone (crude), methoxylamine hydrochloride (1.20 eq) and BH$_3$.THF (1.0 M in THF, 5.00 eq) according to the general procedure B described above. Spectroscopic data: $^1$H NMR (300 MHz, DMSO-$d_6$) δ ppm 2.83-3.00 (m, 2 H) 4.11 (t, J=7.33 Hz, 1 H) 7.34-7.48 (m, 2 H) 7.75 (dd, J=20.96, 11.58 Hz, 2 H) 8.45-8.52 (m, 1 H) 8.53-8.58 (m, J=6.45 Hz, 2 H) 8.79-8.80 (m, 1 H).

1-(2-Fluoro-ethyl)-3-[2-(2-fluoro-phenyl)-1-pyridin-3-yl-ethyl]-urea: The title urea was obtained from 2-(2-fluoro-phenyl)-1-pyridin-3-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.99 (m, 2 H) 3.15 (q, J=5.37 Hz, 1 H) 3.24 (q, J=5.57 Hz, 1 H) 4.21 (t, J=4.98 Hz, 1 H) 4.37 (t, J=5.13 Hz, 1 H) 4.94 (q, J=7.72 Hz, 1 H) 6.12 (t, J=5.86 Hz, 1 H) 6.67 (d, J=8.21 Hz, 1 H) 7.02-7.14 (m, 2 H) 7.16-7.27 (m, 2 H) 7.30 (dd, J=7.92, 4.69 Hz, 1 H) 7.63 (dt, J=7.92, 1.91 Hz, 1 H) 8.36-8.47 (m, 2 H).

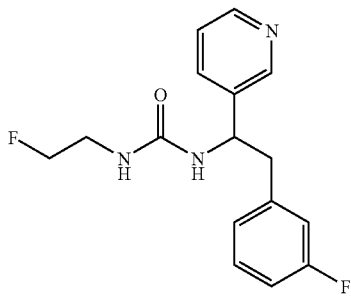

Synthesis of 1-(2-fluoro-ethyl)-3-[2-(3-fluoro-phenyl)-1-pyridin-3-yl-ethyl]-urea The title compound was generated from commercially available nicotinic acid ethyl ester and (3-fluoro-phenyl)-acetonitrile according to the general procedure D described above. The intermediates 2-(3-fluoro-phenyl)-1-pyridin-3-yl-ethanone and 2-(3-fluoro-phenyl)-1-pyridin-3-yl-ethylamine were isolated and characterized.

2-(3-Fluoro-phenyl)-1-pyridin-3-yl-ethanone: The title ketone was obtained from nicotinic acid ethyl ester (10.00 g, 66.16 mmol), (3-fluoro-phenyl)-acetonitrile (9.12 g, 67.49 mmol), sodium ethoxide (50.00 mL, 21 wt. % in EtOH, 0.13 mol) and hydrobromic acid (48%, 80.00 mL) according to the protocols as outlined in general procedure D described above. Spectroscopic data: $^1$H NMR (300 MHz, DMSO-$d_6$) δ ppm 4.06 (s, 2 H) 7.17-7.12 (m, 6 H) 7.40-7.47 (m, 2 H).

2-(3-Fluoro-phenyl)-1-pyridin-3-yl-ethylamine: The intermediate oxime was prepared from 2-(3-fluoro-phenyl)-1-pyridin-3-yl-ethanone (crude) and methoxylamine hydrochloride (6.50 g, 77.83 mmol) according to the protocol described in general procedure B. The oxime was then dissolved in acetic acid (10.00 mL) and Pd/C (0.80 g) was added. The reaction mixture was hydrogenated under 50 psi for 14 hours, then filtered and concentrated. The residue was basified with 5M sodium hydroxide and extracted with methylene chloride. The combined organic phases were dried over potassium carbonate and concentrated to yield the title compound. Spectroscopic data: $^1$H NMR (300 MHz, DMSO-$d_6$) δ ppm 2.83 ((dd, J=7.04, 3.22 Hz, 2 H) 4.07 (t, J=7.04 Hz, 1 H) 6.96-7.08 (m, 2 H) 7.11 (td, J=5.86, 2.64 Hz, 1 H) 7.14-7.23 (m, 1 H) 7.27 (dd, J=7.48, 5.13 Hz, 1 H) 7.70 (ddd, J=7.77, 2.20, 2.05 Hz, 1 H) 8.36 (dd, J=4.84, 1.61 Hz, 1 H) 8.41 (t, J=3.08 Hz, 1 H).

1-(3-Fluoro-ethyl)-3-[2-(3-fluoro-phenyl)-1-pyridin-3-yl-ethyl]-urea: The title compound was generated from 2-(3-fluoro-phenyl)-1-pyridin-3-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.94 (d, J=7.62 Hz, 2 H) 3.15 (q, J=5.28 Hz, 1 H) 3.20-3.29 (m, 1 H) 4.21 (t, J=4.98 Hz, 1 H) 4.37 (t, J=5.13 Hz, 1 H) 4.88 (q, J=7.62 Hz, 1 H) 6.09 (t, J=5.57 Hz, 1 H) 6.61 (d, J=8.21 Hz, 1 H) 6.99-7.10 (m, 2 H) 7.12-7.26 (m, 2 H) 7.27-7.39 (m, 1 H) 7.61-7.76 (m, 1 H) 8.38-8.49 (m, 2 H).

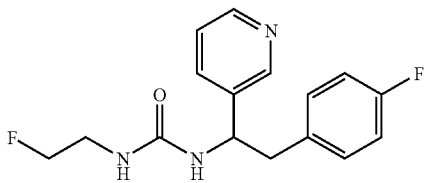

Synthesis of 1-(2-fluoro-ethyl)-3-[2-(4-fluoro-phenyl)-1-pyridin-3-yl-ethyl]-urea The title compound was generated from commercially available nicotinic acid ethyl ester and (4-fluoro-phenyl)-acetonitrile according to the general procedure D described above. The intermediates 2-(4-fluoro-phenyl)-1-pyridin-3-yl-ethanone and 2-(2-fluoro-phenyl)-1-pyridin-3-yl-ethylamine were isolated and characterized.

2-(4-Fluoro-phenyl)-1-pyridin-3-yl-ethanone: The title ketone was obtained from nicotinic acid ethyl ester (10.00 g, 66.16 mmol), (4-fluoro-phenyl)-acetonitrile (9.12 g, 67.49 mmol), sodium ethoxide (50.00 mL, 21 wt. % in EtOH, 133.93 mmol) and hydrobromic acid (48%, 80.00 mL) according to the protocols as outlined in general procedure D described above. Spectroscopic data: $^1$H NMR (300 MHz, DMSO-$d_6$) δ ppm 4.46 (s, 2 H) 7.07-7.19 (m, 2 H) 7.25-7.37 (m, 2 H) 7.56 (dd, J=8.06, 4.84 Hz, 1 H) 8.34 (dt, J=8.14, 1.94 Hz, 1 H) 8.79 (dd, J=4.69, 1.47 Hz, 1 H) 9.20 (d, J=2.05 Hz, 1 H).

2-(4-Fluoro-phenyl)-1-pyridin-3-yl-ethylamine: The title amine was obtained from 2-(4-fluoro-phenyl)-1-pyridin-3-yl-ethanone (crude), methoxylamine hydrochloride (6.00 g, 71.84 mmol) and BH$_3$.THF (1.0 M in THF, 100.00 mL, 0.10 mol) according to the general procedure B described above. Spectroscopic data: $^1$H NMR (300 MHz, DMSO-$d_6$) δ ppm 2.85 (dd, J=7.18, 3.37 Hz, 2 H) 4.07 (t, J=7.04 Hz, 1 H) 7.01-7.15 (m, 3 H) 7.28-7.31 (m, 2 H) 7.70-7.74 (m, 1 H) 8.37-8.43 (m, 2 H).

1-(2-Fluoro-ethyl)-3-[2-(4-fluoro-phenyl)-1-pyridin-3-yl-ethyl]-urea: The title urea was obtained from 2-(4-fluoro-phenyl)-1-pyridin-3-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.94 (d, J=7.33 Hz, 2 H) 3.07-3.19 (m, 1 H) 3.20-3.28 (m, 1 H) 4.22 (t, J=5.13 Hz, 1 H) 4.37 (t, J=4.98 Hz, 1 H) 4.88 (q, J=7.62 Hz, 1 H) 6.10 (t, J=5.72 Hz, 1 H) 6.61 (d, J=8.21 Hz, 1 H) 6.96-7.10 (m, 2 H) 7.10-7.21 (m, 2 H) 7.22-7.38 (m, 1 H) 7.59-7.73 (m, 1 H) 8.40 (ddd, J=11.87, 7.18, 1.76 Hz, 2 H).

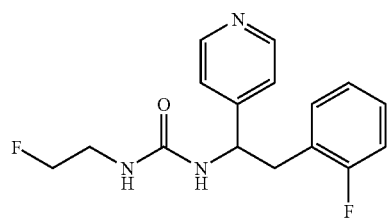

Synthesis of 1-(2-fluoro-ethyl)-3-[2-(2-fluoro-phenyl)-1-pyridin-4-yl-ethyl]-urea The title compound was generated from commercially available isonicotinic acid ethyl ester and (2-fluoro-phenyl)-acetonitrile according to the general procedure D described above. The intermediates 2-(2-fluoro-phenyl)-1-pyridin-4-yl-ethanone and 2-(2-fluoro-phenyl)-1-pyridin-4-yl-ethylamine were isolated and characterized.

2-(2-Fluoro-phenyl)-1-pyridin-4-yl-ethanone: The title ketone was obtained from isonicotinic acid ethyl ester (10.00 g, 66.16 mmol), (2-fluoro-phenyl)-acetonitrile (9.00 g, 66.60 mmol), sodium ethoxide (50.00 mL, 21 wt. % in EtOH, 0.13 mol) and hydrobromic acid (48%, 70.00 mL) according to the protocols as outlined in general procedure D described above. Spectroscopic data: $^1$H NMR (300 MHz, DMSO-$d_6$) δ ppm 4.54 (s, 2 H) 7.12-7.24 (m, 2 H) 7.25-7.39 (m, 2 H) 7.90-7.94 (m, 2 H) 8.83-8.87 (m, 2 H).

2-(2-Fluoro-phenyl)-1-pyridin-4-yl-ethylamine: The intermediate oxime was prepared from 2-(2-fluoro-phenyl)-1-pyridin-4-yl-ethanone (crude) and methoxylamine hydrochloride (6.50 g, 77.83 mmol) according to the protocol described in general procedure B. The oxime was then dissolved in trifluoroacetic acid (30.00 mL) and Pd/C (0.80 g) was added. The reaction mixture was hydrogenated under 50 psi for 14 hours, then filtered and concentrated. The residue was basified with 5M sodium hydroxide and extracted with methylene chloride. The combined organic phases were dried over potassium carbonate and concentrated to yield the title compound. Spectroscopic data: $^1$H NMR (300 MHz, DMSO-$d_6$) δ ppm 2.83-3.00 (m, 2 H) 4.11 (t, J=7.33 Hz, 1 H) 7.34-7.48 (m, 2 H) 7.75 (dd, J=20.96, 11.58 Hz, 2 H) 8.45-8.52 (m, 1 H) 8.53-8.58 (m, J=6.45 Hz, 2 H) 8.79-8.80 (m, 1 H).

1-(2-Fluoro-ethyl)-3-[2-(2-fluoro-phenyl)-1-pyridin-4-yl-ethyl]-urea: The title urea was obtained from 2-(2-fluoro-phenyl)-1-pyridin-4-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.87-3.02 (m, 2 H) 3.15 (q, J=5.18 Hz, 1 H) 3.20-3.29 (m, 1 H) 4.21 (t, J=4.84 Hz, 1 H) 4.37 (t, J=4.98 Hz, 1H) 4.84-4.98 (m, 1 H) 6.16 (t, J=5.42 Hz, 1 H) 6.67 (d, J=8.21 Hz, 1 H) 7.02-7.15 (m, 2 H) 7.20 (s, 1H) 7.22 (d, J=2.35 Hz, 3 H) 8.46 (d, J=5.28 Hz, 2 H).

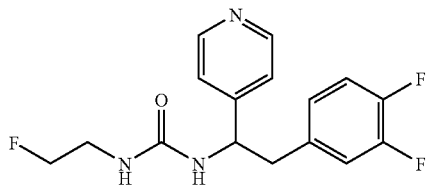

Synthesis of 1-[2-(3,4-difluoro-phenyl)-1-pyridin-4-yl-ethyl]-3-(2-fluoro-ethyl)-urea The title compound was generated from commercially available isonicotinic acid ethyl ester and (3,4-difluoro-phenyl)-acetonitrile according to the general procedure D described above. The intermediates 2-(3,4-difluoro-phenyl)-1-pyridin-4-yl-ethanone and 2-(3,4-difluoro-phenyl)-1-pyridin-4-yl-ethylamine were isolated and characterized.

2-(3,4-Difluoro-phenyl)-1-pyridin-4-yl-ethanone: The title ketone was obtained from isonicotinic acid ethyl ester (10.00 g, 66.16 mmol), (3,4-difluoro-phenyl)-acetonitrile (9.12 g, 59.56 mmol), sodium ethoxide (50.00 mL, 21 wt. % in EtOH, 133.93 mmol) and hydrobromic acid (48%, 80.00 mL) according to the protocols as outlined in general procedure D described above. Spectroscopic data: $^1$H NMR (300 MHz, DMSO-$d_6$) δ ppm 4.51 (s, 2 H) 7.02-7.14 (m, 1 H) 7.32-7.44 (m, 2 H) 7.91 (d, J=4.69 Hz, 2 H) 8.85 (d, J=4.69 Hz, 2 H).

2-(3,4-Difluoro-phenyl)-1-pyridin-4-yl-ethylamine: The intermediate oxime was prepared from 2-(3,4-fluoro-phenyl)-1-pyridin-4-yl-ethanone (crude) and methoxylamine hydrochloride (1.5 eq) according to the protocol described in general procedure B. The oxime was then dissolved in trifluoroacetic acid (30.00 mL) and Pd/C (0.80 g) was added. The reaction mixture was hydrogenated under 50 psi for 14 hours, then filtered and concentrated. The residue was basified with 5M sodium hydroxide and extracted with methylene chloride. The combined organic phases were dried over potassium carbonate and concentrated to yield the title compound. Spectroscopic data: $^1$H NMR (300 MHz, DMSO-$d_6$) δ ppm 3.10-3.31 (m, 2 H) 4.71 (t, J=6.74 Hz, 1 H) 7.54-7.56 (m, 1 H) 7.87-7.92 (m, 1 H) 8.35-8.41 (m, 1 H) 8.69 (d, J=6.16 Hz, 2 H) 8.84-8.87 (m, 2 H).

1-[2-(3,4-Difluoro-phenyl)-1-pyridin-4-yl-ethyl]-3-(2-fluoro-ethyl)-urea: The title urea was obtained from 2-(3,4-difluoro-phenyl)-1-pyridin-4-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.85-3.00 (m, 2 H) 3.15 (q, J=5.28 Hz, 1 H) 3.24 (q, J=5.37 Hz, 1 H) 4.21 (t, J=4.98 Hz, 1 H) 4.37 (t, J=5.13 Hz, 1 H) 4.89 (td, J=8.72, 5.72 Hz, 1 H) 6.13 (t, J=5.72 Hz, 1 H) 6.61 (d, J=8.50 Hz, 1 H) 7.00 (ddd, J=6.30, 4.25, 2.35 Hz, 1 H) 7.21-7.34 (m, 4 H) 8.42-8.55 (m, 2 H).

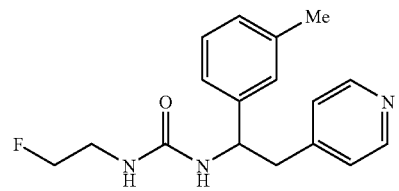

Synthesis of 1-(2-fluoro-ethyl)-3-(2-pyridin-4-yl-1-m-tolyl-ethyl)-urea

The title compound was generated from commercially available 3-methyl-benzoyl chloride and 4-methylpyridine according to the general procedure B described above. The intermediates 2-pyridin-4-yl-1-m-tolyl-ethanone and 2-pyridin-4-yl-1-m-tolyl-ethylamine were isolated and characterized.

2-Pyridin-4-yl-1-m-tolyl-ethanone: The title ketone was obtained from 3-methyl-N-methoxy-N-methyl-benzamide (30.00 mmol, crude) and pyridine-4-ylmethyllithium (prepared from LDA (2.0 M in THF, 18.00 mL, 36 mmol), and 4-methylpyridine (3.00 mL, 30.83 mmol) in THF at 0° C. for 60 min) according to the protocols as outlined in general procedure B described above. Spectroscopic data: $^1$H NMR (300 MHz, DMSO-d$_6$) δ ppm 2.31 (s, 3 H) 4.53 (s, 2 H) 7.16-7.31 (m, 1 H) 7.48-7.63 (m, 1 H) 7.71-7.84 (m, 2 H) 7.96-8.08 (m, 1 H) 8.37-8.47 (m, 1 H) 8.47-8.55 (m, 2 H).

2-Pyridin-4-yl-1-m-tolyl-ethylamine: The intermediate oxime was prepared from 2-pyridin-4-yl-1-m-tolyl-ethanone (crude) and methoxylamine hydrochloride (8.00 g, 95.78 mmol) according to the protocol described in general procedure B. The oxime was then dissolved in trifluoroacetic acid (30.00 mL) and Pd/C (0.80 g) was added. The reaction mixture was hydrogenated under 50 psi for 14 hours, then filtered and concentrated. The residue was basified with 5M sodium hydroxide and extracted with methylene chloride. The combined organic phases were dried over potassium carbonate and concentrated to yield the title compound. Spectroscopic data: $^1$H NMR (300 MHz, DMSO-d$_6$) δ ppm 2.27 (s, 3H) 2.89 (d, J=7.04 Hz, 2 H) 4.12 (t, 1 H) 7.10-7.22 (m, 1 H) 7.39 (ddd, J=7.77, 4.25, 1.47 Hz, 2 H) 7.75-7.82 (m, 1H) 8.41 (td, J=4.98, 2.05 Hz, 2 H) 8.58 (dd, J=5.86, 1.76 Hz, 2 H).

1-(2-Fluoro-ethyl)-3-(2-pyridin-4-yl-1-m-tolyl-ethyl)-urea: The title urea was obtained from 2-pyridin-4-yl-1-m-tolyl-ethylamine (4.40 g, crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.27 (s, 3 H) 2.88-3.01 (m, 2 H) 3.15 (q, J=5.28 Hz, 1 H) 3.24 (q, J=5.28 Hz, 1 H) 4.21 (t, J=5.13 Hz, 1 H) 4.37 (t, J=4.98 Hz, 1 H) 4.84-4.96 (m, 1 H) 6.02 (t, J=5.86 Hz, 1 H) 6.51 (d, J=8.50 Hz, 1 H) 7.04 (dd, J=13.34, 8.36 Hz, 2 H) 7.10 (s, 1 H) 7.12-7.20 (m, 3 H) 8.31-8.43 (m, 2 H).

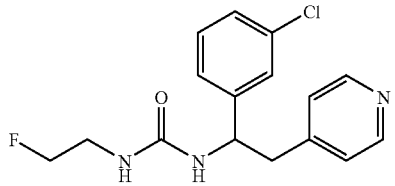

Synthesis of 1-[1-(3-chloro-phenyl)-2-pyridin-4-yl-ethyl]-3-(2-fluoro-ethyl)-urea The title compound was generated from commercially available 3-chloro-benzoyl chloride and 4-methylpyridine according to the general procedure B described above. The intermediates 1-(3-chloro-phenyl)-2-pyridin-4-yl-ethanone and 1-(3-chloro-phenyl)-2-pyridin-4-yl-ethylamine were isolated and characterized.

1-(3-Chloro-phenyl)-2-pyridin-4-yl-ethanone[43]: The title ketone was obtained from 3-chloro-N-methoxy-N-methyl-benzamide (30.00 mmol, crude) and pyridine-4-ylmethyl-lithium (prepared from LDA (2.0 M in THF, 18.00 mL, 36.00 mmol), and 4-methylpyridine (3.00 mL, 30.83 mmol) in THF at 0° C. for 60 min) according to the protocols as outlined in general procedure B described above. Spectroscopic data: $^1$H NMR (300 MHz, DMSO-d$_6$) δ ppm 4.50 (s, 2 H) 7.27 (d, J=5.57 Hz, 2 H) 7.56 (t, J=7.77 Hz, 1 H) 7.71 (d, J=7.92 Hz, 1 H) 7.98 (d, J=7.92 Hz, 1 H) 8.03 (s, 1 H) 8.49 (d, J=1.47 Hz, 1 H) 8.51 (s, 1 H).

[43] Stefanidis, Dimitrios; Bunting, John W. *J. Am. Chem. Soc.* 1990, 112, 3163-3168.

1-(3-Chloro-phenyl)-2-pyridin-4-yl-ethylamine: The title amine was obtained from 1-(3-chloro-phenyl)-2-pyridin-4-yl-ethanone (6.40 g, 27.62 mmol), methoxylamine hydrochloride (5.00 g, 59.87 mmol) and BH$_3$.THF (1.0 M in THF, 50.00 mL, 50.00 mmol) according to the general procedure B described above. $^1$H NMR (300 MHz, Solvent) δ ppm 2.84 (d, J=7.04 Hz, 2 H) 4.10 (t, J=9.01 Hz, 1 H) 7.14-7.21 (m, 2H) 7.24-7.31 (m, 2 H) 7.39-7.46 (m, 1 H) 7.63 (dt, J=7.26, 1.65 Hz, 1 H) 8.43 (ddd, J=12.46, 4.40, 1.61 Hz, 2 H).

1-[1-(3-Chloro-phenyl)-2-pyridin-4-yl-ethyl]-3-(2-fluoro-ethyl)-urea: The title urea was obtained from 1-(3-chloro-phenyl)-2-pyridin-4-yl-ethylamine (6.00 g, crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.87-3.02 (m, 2 H) 3.15 (q, J=5.28 Hz, 1 H) 3.24 (q, J=5.28 Hz, 1 H) 4.21 (t, J=4.98 Hz, 1 H) 4.37 (t, J=5.13 Hz, 1 H) 4.89-5.03 (m, 1 H) 6.07 (t, J=5.57 Hz, 1 H) 6.61 (d, J=8.80 Hz, 1 H) 7.19 (d, J=5.57 Hz, 2 H) 7.23-7.38 (m, 4 H) 8.41 (d, J=5.57 Hz, 2 H).

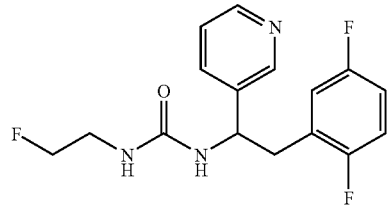

Synthesis of 1-[2-(2,5-difluoro-phenyl)-1-pyridin-3-yl-ethyl]-3-(2-fluoro-ethyl)-urea The title compound was generated from commercially available nicotinic acid ethyl ester and (2,5-difluoro-phenyl)-acetonitrile according to the general procedure D described above. The intermediates 2-(2,5-difluoro-phenyl)-1-pyridin-3-yl-ethanone and 2-(2,5-difluoro-phenyl)-1-pyridin-3-yl-ethylamine were isolated and characterized.

2-(2,5-Difluoro-phenyl)-1-pyridin-3-yl-ethanone: The title ketone was obtained from nicotinic acid ethyl ester (10.00 g, 66.16 mmol), (2,5-difluoro-phenyl)-acetonitrile (9.12 g, 67.49 mmol), sodium ethoxide (50.00 mL, 21 wt. % in EtOH, 133.93 mmol) and hydrobromic acid (48%, 80.00 mL) according to the protocols as outlined in general procedure D described above. Spectroscopic data: $^1$H NMR (300 MHz, DMSO-d$_6$) δ ppm 4.57 (d, J=1.47 Hz, 2 H) 7.14-7.30 (m, 3 H) 7.62 (dd, J=7.62, 5.28 Hz, 1 H) 8.39 (ddd, J=8.21, 2.05, 1.76 Hz, 1 H) 8.85 (dd, J=4.84, 1.61 Hz, 1 H) 9.24 (d, J=1.47 Hz, 1 H).

2-(2,5-Difluoro-phenyl)-1-pyridin-3-yl-ethylamine: The title amine was obtained from 2-(2,5-difluoro-phenyl)-1-pyridin-3-yl-ethanone (crude), methoxylamine hydrochloride (1.2 eq) and BH$_3$.THF (1.0 M in THF, 5.00 eq) according to the general procedure B described above. Spectroscopic data: $^1$H NMR (300 MHz, DMSO-d$_6$) δ ppm 2.82-2.98 (m, 2 H) 4.12 (t, J=7.18 Hz, 1 H) 7.00-7.15 (m, 1 H) 7.29 (dd, J=7.77, 4.84 Hz, 1 H) 7.35-7.42 (m, 1 H) 7.68-7.82 (m, 2 H) 8.40 (td, J=5.28, 1.76 Hz, 1 H) 8.58 (ddd, J=3.88, 1.83, 1.61 Hz, 1 H).

1-[2-(2,5-Difluoro-phenyl)-1-pyridin-3-yl-ethyl]-3-(2-fluoro-ethyl)-urea: The title urea was obtained from 2-(2,5-difluoro-phenyl)-1-pyridin-3-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.99 (d, J=7.33 Hz, 2 H) 3.17 (s, 1 H) 3.25 (d, J=4.98 Hz, 1 H) 4.21 (s, 1 H) 4.37 (s, 1 H) 4.97 (s, 1 H) 6.13 (s, 1 H) 6.67 (s, 1 H) 7.10 (s, 3 H) 7.32 (s, 1 H) 7.66 (s, 1 H) 8.43 (s, 2 H).

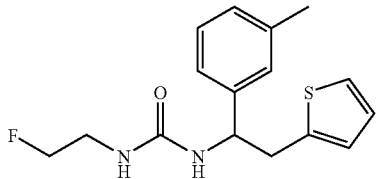

Synthesis of 1-(2-fluoro-ethyl)-3-(2-thiophen-2-yl-1-m-tolyl-ethyl)-urea

The title compound was generated from commercially available thiophen-2-yl-acetyl chloride and m-tolylmagnesium bromide according to the general procedure B described above. The intermediates 2-thiophen-2-yl-1-m-tolyl-ethanone and 2-thiophen-2-yl-1-m-tolyl-ethylamine were isolated and characterized.

2-Thiophen-2-yl-1-m-tolyl-ethanone: The title ketone was obtained from thiophen-2-yl-acetyl chloride (25.00 g, 155.65 mmol), N,O-dimethyl-hydroxylamine (20.00 g, 205.04 mmol), Et$_3$N (38.00 mL, 0.27 mol), catalytic amount of DMAP and m-tolylmagnesium bromide (1.0 M in THF, 200.00 mL, 0.20 mol) according to the protocols as outlined in general procedure B described above. Spectroscopic data: $^1$H NMR (300 MHz, DMSO-$d_6$) δ ppm 2.37 (s, 3 H) 4.61 (s, 2 H) 6.90-7.04 (m, 2 H) 7.10-7.26 (m, 1 H) 7.34-7.48 (m, 2 H) 7.81-7.86 (m, 2 H).

2-Thiophen-2-yl-1-m-tolyl-ethylamine: The title amine was obtained from 2-thiophen-2-yl-1-m-tolyl-ethanone (5.00 g, 23.12 mmol), methoxylamine hydrochloride (3.40 g, 40.71 mmol) and BH$_3$.THF (1.0 M in THF, 60.00 mL, 60.00 mmol) according to the general procedure B described above. Spectroscopic data: $^1$H NMR (300 MHz, DMSO-$d_6$) δ ppm 2.26 (s, 3 H) 3.01 (dd, J=6.74, 4.10 Hz, 2 H) 3.96 (t, J=6.89 Hz, 1 H) 6.75 (d, J=3.22 Hz, 1 H) 6.87 (dd, J=5.13, 3.37 Hz, 1 H) 6.99 (d, J=6.74 Hz, 1 H) 7.08-7.18 (m, 3 H) 7.24-7.28 (m, 1 H).

1-(2-Fluoro-ethyl)-3-(2-thiophen-2-yl-1-m-tolyl-ethyl)-urea: The title urea was obtained from 2-thiophen-2-yl-1-m-tolyl-ethylamine (crude, taken from the previous step without further purification), diimidazole carbonyl (2.30 g, 14.18 mmol), fluoroethyl amine hydrochloride (1.60 g, 90% purity, 14.47 mmol) and diisopropylethyl amine (4.50 mL, 25.84 mmol) according to the protocols as outlined in general procedure A above. Spectroscopic data: $^1$H NMR (300 MHz, DMSO-$d_6$) δ ppm 2.27 (s, 3 H) 3.10-3.25 (m, 3 H) 3.25-3.38 (m, 1 H) 4.25 (t, J=4.98 Hz, 1 H) 4.41 (t, J=4.98 Hz, 1 H) 4.83 (q, J=7.72 Hz, 1 H) 6.12 (t, J=5.57 Hz, 1 H) 6.53 (d, J=8.50 Hz, 1 H) 6.77 (s, 1 H) 6.87 (dd, J=4.98, 3.22 Hz, 1 H) 6.97-7.11 (m, 3H) 7.17 (t, J=7.48 Hz, 1 H) 7.26 (d, J=4.69 Hz, 1 H).

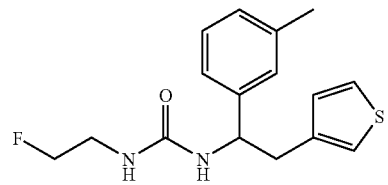

Synthesis of 1-(2-fluoro-ethyl)-3-(2-thiophen-2-yl-1-m-tolyl-ethyl)-urea

The title compound was generated from commercially available thiophen-3-yl-acetic acid and m-tolylmagnesium bromide according to the general procedure C described above. The intermediates 2-thiophen-3-yl-1-m-tolyl-ethanone and 2-thiophen-3-yl-1-m-tolyl-ethylamine were isolated and characterized.

2-Thiophen-3-yl-1-m-tolyl-ethanone: The title ketone was obtained from thiophen-3-yl-acetic acid (25.00 g, 175.83 mmol), thionyl chloride (15.00 mL, 205.64 mmol), N,O-dimethyl-hydroxylamine (20.00 g, 205.04 mmol), Et$_3$N (38.00 mL, 0.27 mol), catalytic amount of DMAP and m-tolylmagnesium bromide (1.0 M in THF, 200.00 mL, 200.00 mmol) according to the protocols as outlined in general procedure C described above. $^1$H NMR (300 MHz, Solvent) δ ppm 2.36 (s, 3 H) 4.36 (s, 2 H) 7.00 (d, J=4.98 Hz, 1 H) 7.14-7.24 (m, 2 H) 7.36-7.47 (m, 2 H) 7.77-7.90 (m, 2 H).

2-Thiophen-3-yl-1-m-tolyl-ethylamine: The title amine was obtained from 2-thiophen-3-yl-1-m-tolyl-ethanone (5.00 g, 23.12 mmol), methoxylamine hydrochloride (3.40 g, 40.71 mmol) and BH$_3$.THF (1.0 M in THF, 60.00 mL, 60.00 mmol) according to the general procedure C described above. Spectroscopic data: $^1$H NMR (300 MHz, DMSO-$d_6$) δ ppm 2.26 (s, 3 H) 2.74-2.88 (m, 2 H) 4.00 (dd, J=7.48, 6.30 Hz, 1 H) 6.90 (d, J=4.98 Hz, 1 H) 6.98 (d, J=6.16 Hz, 1 H) 7.06-7.17 (m, 2 H) 7.32-7.41 (m, 2 H) 8.56 (dd, J=5.86, 1.76 Hz, 1 H).

1-(2-Fluoro-ethyl)-3-(2-thiophen-3-yl-1-m-tolyl-ethyl)-urea: The title urea was obtained from 2-thiophen-3-yl-1-m-tolyl-ethylamine (crude, taken from the previous step without further purification), diimidazole carbonyl (1.65 g, 10.17 mmol), fluoroethyl amine hydrochloride (1.10 g, 90% purity, 9.95 mmol) and diisopropylethyl amine (3.00 mL, 17.22 mmol) according to the protocols as outlined in general procedure A above. Spectroscopic data: $^1$H NMR (300 MHz, DMSO-$d_6$) δ ppm 2.26 (s, 3 H) 2.92 (d, J=7.04 Hz, 2H) 3.18 (q, J=4.98 Hz, 1 H) 3.23-3.37 (m, 1 H) 4.24 (t, J=4.98 Hz, 1 H) 4.40 (t, J=4.98 Hz, 1 H) 4.84 (q, J=7.52 Hz, 1 H) 6.07 (t, J=5.57 Hz, 1 H) 6.47 (d, J=8.21 Hz, 1 H) 6.87 (d, J=4.98 Hz, 1 H) 6.98-7.10 (m, 4 H) 7.16 (t, J=7.48 Hz, 1 H) 7.37 (dd, J=4.40, 2.93 Hz, 1 H).

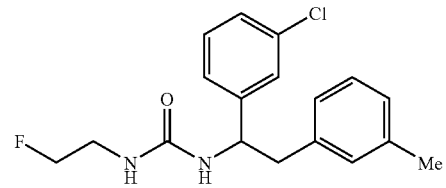

Synthesis of 1-[1-(3-chloro-phenyl)-2-m-tolyl-ethyl]-3-(2-fluoro-ethyl)-urea

The title compound was generated from commercially available m-tolyl-acetic acid according to the general procedure C described above. The intermediates 1-(3-chloro-phenyl)-2-m-tolyl-ethanone and 1-(3-chloro-phenyl)-2-m-tolyl-ethylamine were isolated and characterized.

1-(3-Chloro-phenyl)-2-m-tolyl-ethanone: The title ketone was obtained from o-tolyl-acetic acid (5.00 g, 33.30 mmol), thionyl chloride (5.00 mL, 68.55 mmol), N,O-dimethyl-hydroxylamine (5.00 g, 51.26 mmol), Et$_3$N (20.00 mL, 0.14 mol), catalytic amount of DMAP and 3-chlorophenylmagnesium bromide (0.5 M in THF, 50.00 mL, 25.00 mmol) according to the protocols as outlined in general procedure C described above.

1-(3-Chloro-phenyl)-2-m-tolyl-ethylamine: The title amine was obtained from 1-(3-chloro-phenyl)-2-m-tolyl-ethanone (crude, taken from the previous reaction), methoxylamine hydrochloride (3.50 g, 41.91 mmol) and BH$_3$.THF (1.0 M in THF, 60.00 mL, 60.00 mmol) according to the general procedure C described above. Spectroscopic data: $^1$H NMR (300 MHz, DMSO-d$_6$) δ ppm 2.23 (s, 3 H) 2.66-2.81 (m, 2 H) 4.30 (br s, 1 H), 6.93-7.44 (m, 8 H).

1-[1-(3-Chloro-phenyl)-2-m-tolyl-ethyl]-3-(2-fluoro-ethyl)-urea: The title urea was obtained from 1-(3-chloro-phenyl)-2-o-tolyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-d$_6$) δ ppm 2.26 (s, 3 H), 2.87-2.90 (m, 2 H) 3.16 (q, J=5.08 Hz, 1 H) 3.25 (q, J=5.28 Hz, 1 H) 4.22 (t, J=5.13 Hz, 1 H) 4.37 (t, J=4.98 Hz, 1 H) 4.86 (q, J=7.92 Hz, 1 H) 6.09 (t, J=5.72 Hz, 1 H) 6.60 (d, J=8.50 Hz, 1 H) 7.00-7.12 (m, 4 H) 7.16 (d, J=7.04 Hz, 1 H) 7.22-7.35 (m, 3 H).

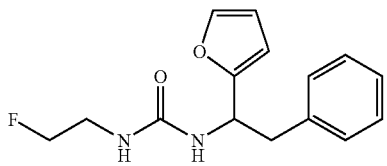

Synthesis of 1-(2-fluoro-ethyl)-3-(1-furan-2-yl-2-phenyl-ethyl)-urea

The title compound was generated from commercially available 2-furoyl chloride and benzylmagnesium bromide according to the general procedure B described above. The intermediates 1-furan-2-yl-2-phenyl-ethanone and 1-furan-2-yl-2-phenyl-ethylamine were isolated and characterized.

1-Furan-2-yl-2-phenyl-ethanone[44]: The title ketone was obtained from 2-furoyl chloride (10.00 mL, 101.43 mmol), N,O-dimethyl-hydroxylamine (15.00 g, 153.78 mmol), Et$_3$N (38.00 mL, 0.27 mol), catalytic amount of DMAP and benzylmagnesium bromide (2.0 M in THF, 100.00 mL, 0.20 mol) according to the protocols as outlined in general procedure B described above. Spectroscopic data: $^1$H

[44] Fontana, Antonella; O'Ferrall, Rory A. More *J. Chem. Soc. Perkin Trans. 2* 1994, 12, 2453-2460. NMR (300 MHz, DMSO-d$_6$) δ ppm 4.14 (s, 2 H) 6.72 (dd, J=3.66, 1.61 Hz, 1 H) 7.14-7.31 (m, 5 H) 7.60 (d, J=3.81 Hz, 1 H) 8.00 (s, 1 H).

1-Furan-2-yl-2-phenyl-ethylamine[45]: The title amine was obtained from 1-furan-2-yl-2-phenyl-ethanone (5.00 g, 26.85 mmol), methoxylamine hydrochloride (3.40 g, 40.71 mmol) and BH$_3$.THF (1.0 M in THF, 60.00 mL, 60.00 mmol) according to the general procedure B described above. Spectroscopic data: $^1$H NMR (300 MHz, DMSO-d$_6$) δ ppm 1.76 (br s, 2 H) 2.80 (dd, J=13.19, 7.62 Hz, 1 H) 2.90-3.02 (m, 1 H) 4.03 (t, J=6.89 Hz, 1 H) 6.11 (d, J=3.22 Hz, 1 H) 6.31 (dd, J=3.08, 1.91 Hz, 1 H) 7.08-7.12 (m, 2 H) 7.14-7.24 (m, 3 H) 7.51 (s, 1 H).

[45] Demir, Ayhan S.; Sesenoglu, Oezge; Uelkue, Dincer; Arici, Cengiz *Helv. Chim. Acta* 2003, 86, 91-105.

1-(2-Fluoro-ethyl)-3-(1-furan-2-yl-2-phenyl-ethyl)-urea: The title urea was obtained from 1-furan-2-yl-2-phenyl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-d$_6$) δ ppm 2.90-3.05 (m, 2 H) 3.19 (q, J=5.28 Hz, 1 H) 3.25-3.34 (m, 1 H) 4.24 (t, J=5.13 Hz, 1 H) 4.40 (t, J=5.13 Hz, 1 H) 4.91-5.01 (m, 1 H) 6.05-6.16 (m, 2 H) 6.32 (dd, J=3.22, 1.76 Hz, 1 H) 6.40 (d, J=8.79 Hz, 1 H) 7.07-7.09 (m, 2 H) 7.14-7.24 (m, 3 H) 7.55 (s, 1 H).

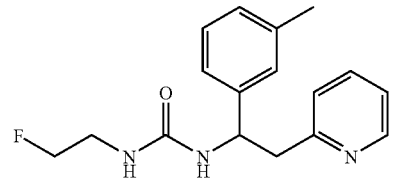

Synthesis of 1-(2-fluoro-ethyl)-3-(2-pyridin-2-yl-1-m-tolyl-ethyl)-urea

The title compound was generated from commercially available 3-methyl-benzoyl chloride and 2-methylpyridine according to the general procedure B described above. The intermediates 1-(3-methyl-phenyl)-2-pyridin-2-yl-ethanone and 1-(3-methyl-phenyl)-2-pyridin-2-yl-ethylamine were isolated and characterized.

1-(3-Methyl-phenyl)-2-pyridin-2-yl-ethanone[46]: The title ketone was obtained from 3-methyl-N-methoxy-N-methyl-benzamide (5.50 g, 30.83 mmol) and pyridine-2-ylmethyl-lithium (prepared from LDA (2.0 M in THF, 20.00 mL, 40.00 mmol), and 3-methylpyridine (3.00 mL, 30.83 mmol) in THF at 0° C. for 60 min) according to the protocols as outlined in general procedure B described above. Spectroscopic data: $^1$H NMR (300 MHz, DMSO-d$_6$) δ ppm 2.35 (s, 3 H) 4.50 (s, 2 H) 7.10-7.43 (m, 5 H) 7.61-7.65 (m, 1 H) 7.71-7.82 (m, 1 H) 8.38-8.46 (m, 1 H).

[46] Kolehmainen, Erkki; Osmialowski, Borys; Nissinen, Maija; Kauppinen, Reijo; Gawinecki, Ryszard *J. Chem. Soc. Perkin Trans. 2* 2000, 11, 2185-2191.

1-(3-Methyl-phenyl)-2-pyridin-2-yl-ethylamine: The title amine was obtained from 1-(3-methyl-phenyl)-2-pyridin-2-yl-ethanone (5.00 g, 23.67 mmol), methoxylamine hydrochloride (3.20 g, 38.31 mmol) and BH$_3$.THF (1.0 M in THF, 100.00 mL, 100.00 mmol) according to the general procedure B described above. Spectroscopic data: $^1$H NMR (300 MHz, DMSO-d$_6$) δ ppm 2.25 (s, 3 H) 2.91 (d, J=1.76 Hz, 2 H) 4.20 (t, J=7.62 Hz, 1 H) 6.97 (d, J=6.74 Hz, 1 H) 7.06-7.18 (m, 5 H) 7.61 (td, J=7.62, 1.76 Hz, 1 H) 8.46-8.47 (m, 1 H).

1-(2-Fluoro-ethyl)-3-(2-pyridin-2-yl-1-m-tolyl-ethyl)-urea: The title urea was obtained from 1-(3-methyl-phenyl)-2-pyridin-3-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.24 (s, 3 H) 3.03 (d, J=7.62 Hz, 2 H) 3.13 (q, J=5.28 Hz, 1 H) 3.22 (q, J=5.37 Hz, 1 H) 4.20 (t, J=5.13 Hz, 1 H) 4.35 (t, J=4.98 Hz, 1 H) 5.05 (q, J=7.52 Hz, 1 H) 6.06 (t, J=5.86 Hz, 1 H) 6.55 (d, J=8.79 Hz, 1 H) 6.99 (dd, J=11.73, 7.62 Hz, 2 H) 7.05 (s, 1 H) 7.10-7.18 (m, 3 H) 7.61 (td, J=7.62, 1.76 Hz, 1 H) 8.45 (d, J=4.69 Hz, 1 H).

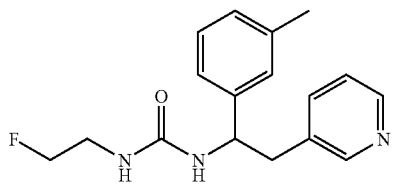

Synthesis of 1-(2-fluoro-ethyl)-3-(2-pyridin-3-yl-1-m-tolyl-ethyl)-urea

The title compound was generated from commercially available 3-methyl-benzoyl chloride and 3-methylpyridine according to the general procedure B described above. The intermediates 1-(3-methyl-phenyl)-2-pyridin-3-yl-ethanone and 1-(3-methyl-phenyl)-2-pyridin-2-yl-ethylamine were isolated and characterized.

1-(3-Methyl-phenyl)-2-pyridin-3-yl-ethanone: The title ketone was obtained from 3-methyl-N-methoxy-N-methyl-benzamide (5.50 g, 30.69 mmol) and pyridine-3-ylmethyl-lithium (prepared from LDA (2.0 M in THF, 20.00 mL, 40.00 mmol), and 3-methylpyridine (3.00 mL, 30.83 mmol) in THF at 0° C. for 60 min) according to the protocols as outlined in general procedure B described above. Spectroscopic data: $^1$H NMR (300 MHz, DMSO-$d_6$) δ ppm 3.22 (s, 3 H) 4.45 (s, 2 H) 7.25 (s, 1 H) 7.37-7.45 (m, 2 H) 7.53-7.69 (m, 2 H) 7.84-7.88 (m, 1 H) 8.34-8.45 (m, 2 H).

1-(3-Methyl-phenyl)-2-pyridin-3-yl-ethylamine: The title amine was obtained from 1-(3-methyl-phenyl)-2-pyridin-3-yl-ethanone (5.00 g, 23.67 mmol), methoxylamine hydrochloride (3.20 g, 38.31 mmol) and BH$_3$.THF (1.0 M in THF, 100.00 mL, 100.00 mmol) according to the general procedure B described above. Spectroscopic data: $^1$H NMR (300 MHz, DMSO-$d_6$) δ ppm 3.22 (s, 3 H) 4.45 (s, 2 H) 6.96-7.26 (m, 6 H) 7.48-7.52 (m, 1 H) 8.26-8.34 (m, 1 H).

1-(2-Fluoro-ethyl)-3-(2-pyridin-3-yl-1-m-tolyl-ethyl)-urea: The title urea was obtained from 1-(3-methyl-phenyl)-2-pyridin-3-yl-ethylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 16.81 mmol) according to the protocols as outlined in general procedure A above. Spectroscopic data: $^1$H NMR (300 MHz, DMSO-$d_6$) δ ppm 2.26 (s, 3 H) 2.84-2.98 (m, 2 H) 3.14 (q, J=5.28 Hz, 1 H) 3.24 (q, J=5.28 Hz, 1 H) 4.20 (t, J=5.13 Hz, 1 H) 4.36 (t, J=5.13 Hz, 1 H) 4.79-4.89 (m, 1 H) 6.03 (t, J=5.72 Hz, 1 H) 6.51 (d, J=8.79 Hz, 1 H) 7.00 (s, 1 H) 7.01-7.10 (m, 2 H) 7.13-7.27 (m, 2 H) 7.50-7.57 (m, 1 H) 8.31 (d, J=1.47 Hz, 1 H) 8.35 (dd, J=4.84, 1.61 Hz, 1H).

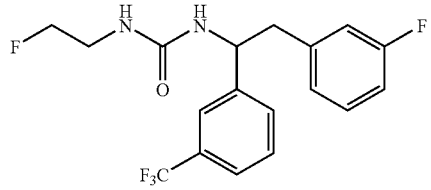

Synthesis of 1-(2-fluoro-ethyl)-3-[2-(3-fluoro-phenyl)-1-(3-trifluoromethyl-phenyl)-ethyl]-urea The title compound was obtained from the commercially available 3-trifluoromethylbenzoic acid methyl ester and 3-fluorophenylacetonitrile according to general procedure D described above. The intermediates 2-(3-fluoro-phenyl)-1-(3-trifluoromethyl-phenyl)-ethanone, 2-(3-fluoro-phenyl)-1-(3-trifluoromethyl-phenyl)-ethanone O-methyl-oxime and 2-(3-fluoro-phenyl)-1-(3-trifluoromethyl-phenyl)-ethylamine were separated and characterized.

2-(3-Fluoro-phenyl)-1-(3-trifluoromethyl-phenyl)-ethanone: 3.44 g of the title compound was obtained from 3-trifluoromethyl-benzoic acid methyl ester (15.00 g, 0.27 mol), (3-fluoro-phenyl)-acetonitrile (9.40 mL, 73.70 mmol), NaOEt (56.00 mL, 28% wt in EtOH, 0.15 mmol) and HBr (48%, 40 mL) according to the protocols as outlined in general procedure D described above. Spectroscopic data: $^1$H NMR (300 MHz, CDCl$_3$) δ 4.34 (s, 2 H), 7.05-7.15 (m, 2 H), 7.21-7.32 (m, 2 H), 7.57-7.66 (m, 1 H), 7.81-7.85 (m, 1 H), 8.21 (d, J=7.92 Hz, 1 H), 8.27-8.32 (m, 1 H).

2-(3-Fluoro-phenyl)-1-(3-trifluoromethyl-phenyl)-ethanone O-methyl-oxime: 2.73 g (72%) of the title compound was obtained from 2-(3-fluoro-phenyl)-1-(3-trifluoromethyl-phenyl)-ethanone (3.44 g, 12.20 mmol), methoxylamine hydrochloride (2.04 g, 24.40 mmol) and pyridine (3.0 mL) according to the protocols as outlined in general procedure D described above. Spectroscopic data: $^1$H NMR (300 MHz, CDCl$_3$) δ 4.04 (s, 3 H), 4.17 (s, 2 H), 6.96-7.23 (m, 4 H), 7.43 (t, J=7.92, 7.04 Hz, 1 H), 7.57 (d, J=7.92 Hz, 1 H), 7.76 (d, J=7.92 Hz, 1 H), 7.98 (s, 1 H).

2-(3-Fluoro-phenyl)-1-(3-trifluoromethyl-phenyl)-ethylamine: To a solution of 2-(3-fluoro-phenyl)-1-(3-trifluoromethyl-phenyl)-ethanone O-methyl-oxime (1.00 g, 3.20 mmol) in Et$_2$O at 0° C. was added LAH (1.0 M in THF, 3.20 mL, 3.20 mmol). The reaction mixture was stirred for a few minutes, and then refluxed for 30 hours. The resulting mixture was cooled to 0° C. and quenched with a few drops of H$_2$O. The mixture was filtered through a pad of celite, concentrated and purified by column chromatography using hexane:EtOAc (1:1) as eluant to give 470 mg of the desired title compound. Spectroscopic data: $^1$H NMR (300 MHz, CDCl$_3$) δ 1.47-1.62 (m, 2 H), 2.84-2.93 (m, 1 H), 2.98-3.07 (m, 1 H), 4.28-4.35 (m, 1 H), 6.99-7.11 (m, 3 H), 7.16-7.27 (m, 1 H), 7.39-7.46 (m, 1 H), 7.52 (t, J=7.62 Hz, 2 H), 7.61 (s, 1H).

1-(2-Fluoro-ethyl)-3-[2-(3-fluoro-phenyl)-1-(3-trifluoromethyl-phenyl)-ethyl]-urea: The title urea was produced from 2-(3-fluoro-phenyl)-1-(3-trifluoromethyl-phenyl)-ethylamine (0.47 g, 1.70 mmol), diimidazole carbonyl (0.27 g, 1.66 mmol), fluoroethyl amine hydrochloride (165.3 mg, 90% purity, 1.50 mmol) and diisopropyl ethyl amine (580 μL, 3.33 mmol) according to the protocols as outlined in general procedure A. Spectroscopic data: $^1$H NMR (300 MHz, DMSO-$d_6$) δ 3.01 (d, J=7.33 Hz, 2 H), 3.19 (q, J=5.28 Hz, 1 H), 3.28 (q, J=5.28 Hz, 1 H), 4.23 (t, J=5.28 Hz, 1 H), 4.40 (t, J=4.98 Hz, 1 H), 5.05 (q, J=8.21, 7.62 Hz, 1 H), 6.17 (t, J=5.57 Hz, 1 H), 6.75 (d, J=8.50 Hz, 1 H), 7.04-7.14 (m, 2 H), 7.19-7.30 (m, 2 H), 7.49-7.61 (m, 4 H).

BIOLOGICAL DATA

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

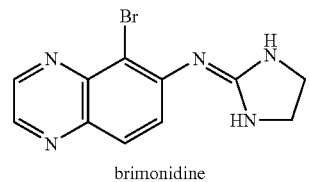

brimonidine

The results of the RSAT assay with several exemplary compounds of the invention are disclosed in Table 1 above together with the chemical formulas of these exemplary compounds. EC$_{50}$ values are nanomolar. NA stands for "not active" at concentrations less than 10 micromolar. IA stands for "intrinsic activity."

| Compound | Alpha 2A | | Alpha 2B | | Alpha 2C | |
|---|---|---|---|---|---|---|
| | EC$_{50}$ | IA | EC$_{50}$ | IA | EC$_{50}$ | IA |
| (structure) | not active | | 33.8 | 0.96 | 345 | 0.32 |
| (structure) | not active | | 29.3 | 0.92 | not active | |
| (structure) | not active | | 606 | 0.63 | not active | |

-continued
| Compound | Alpha 2A | | Alpha 2B | | Alpha 2C | |
|---|---|---|---|---|---|---|
| | EC$_{50}$ | IA | EC$_{50}$ | IA | EC$_{50}$ | IA |
| 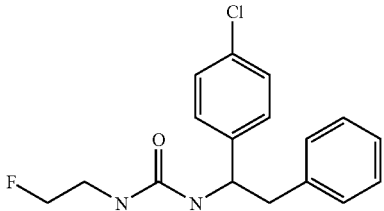 | not active | | 177 | 0.55 | not active | |
| 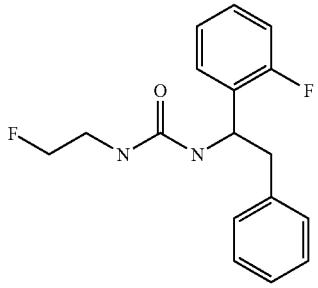 | 2140 | 0.35 | 103 | 0.79 | 101 | 0.31 |
| 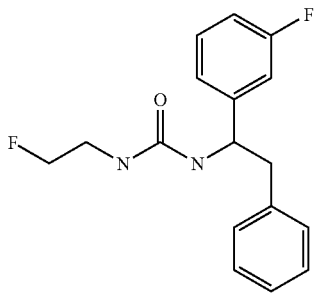 | 836 | 0.31 | 53.5 | 0.96 | 511 | 0.48 |
| 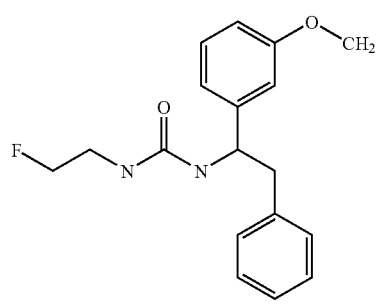 | not active | | 959 | 0.84 | not active | |
| 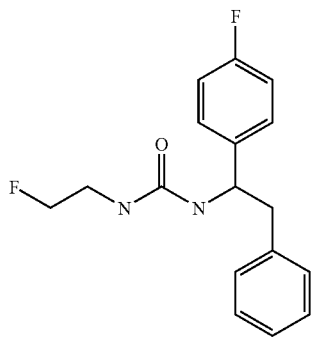 | not active | | 299 | 0.71 | not active | |

-continued

| Compound | Alpha 2A | | Alpha 2B | | Alpha 2C | |
|---|---|---|---|---|---|---|
| | $EC_{50}$ | IA | $EC_{50}$ | IA | $EC_{50}$ | IA |
| [4-methoxyphenyl compound] | not active | | 1060 | 0.3 | not active | |
| [2-methoxyphenyl compound] | not active | | 51.2 | 0.88 | 78.9 | 0.42 |
| [3-bromophenyl compound] | not active | | 173 | 0.86 | not active | |
| [4-methylphenyl compound] | not active | | 218 | 0.53 | not active | |

-continued

| Compound | Alpha 2A | | Alpha 2B | | Alpha 2C | |
|---|---|---|---|---|---|---|
| | EC$_{50}$ | IA | EC$_{50}$ | IA | EC$_{50}$ | IA |
| *(3-methylphenyl compound)* | not active | | 29.8 | 0.91 | not active | |
| *(3,4-dichlorophenyl compound)* | not active | | 488 | 0.69 | not active | |
| *(2-chlorophenyl compound)* | not active | | 407 | 0.64 | 700 | 0.34 |
| *(cyclohexyl compound)* | not active | | 640 | 0.33 | not active | |
| *(cyclopentyl compound)* | not active | | 378 | 0.6 | not active | |

| Compound | Alpha 2A | | Alpha 2B | | Alpha 2C | |
|---|---|---|---|---|---|---|
| | $EC_{50}$ | IA | $EC_{50}$ | IA | $EC_{50}$ | IA |
| 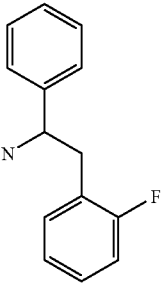 | not active | | 12.9 | 0.96 | not active | |
| 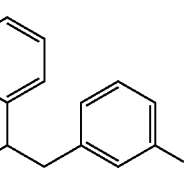 | not active | | 26 | 0.95 | not active | |
| 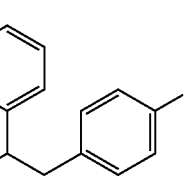 | not active | | 51.3 | 0.93 | not active | |
| 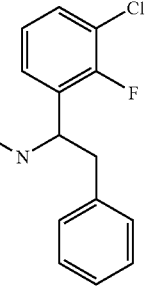 | not active | | 138 | 1.0 | not active | |
| 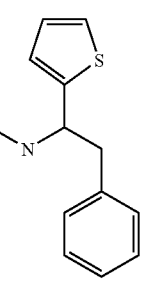 | 346 | 0.35 | 28.5 | 0.99 | 119 | 0.35 |
| 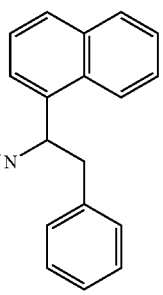 | not active | | 160 | 0.77 | not active | |

-continued
| Compound | Alpha 2A | | Alpha 2B | | Alpha 2C | |
|---|---|---|---|---|---|---|
| | EC$_{50}$ | IA | EC$_{50}$ | IA | EC$_{50}$ | IA |
| 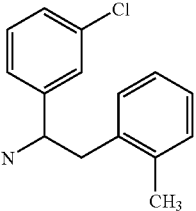 | not active | | 26.8 | 0.94 | 787 | 0.38 |
| 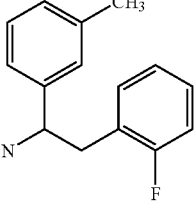 | not active | | 13.8 | 1.02 | not active | |
| 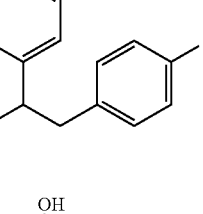 | not active | | 42.9 | 0.88 | not active | |
| 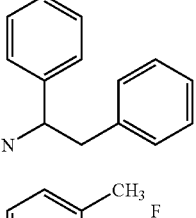 | not active | | 146 | 0.82 | not active | |
| 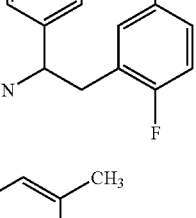 | not active | | 21.3 | 1.02 | not active | |
| 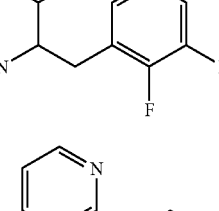 | not active | | 20.5 | 1.02 | not active | |
| 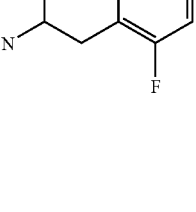 | not active | | 747 | 0.78 | not active | |

-continued
| Compound | Alpha 2A | | Alpha 2B | | Alpha 2C | |
|---|---|---|---|---|---|---|
| | EC$_{50}$ | IA | EC$_{50}$ | IA | EC$_{50}$ | IA |
| 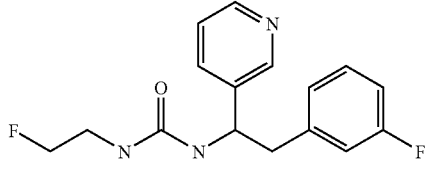 | not active | | 1990 | 0.41 | not active | |
| 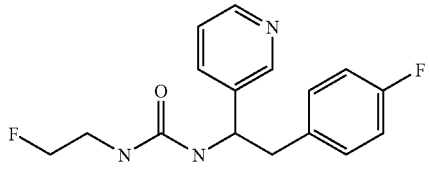 | not active | | 2780 | 0.49 | not active | |
| 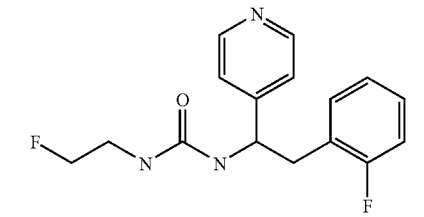 | not active | | 2120 | 0.53 | not active | |
| 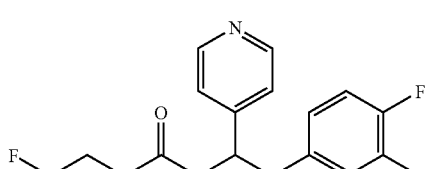 | not active | | 3620 | 0.44 | not active | |
| 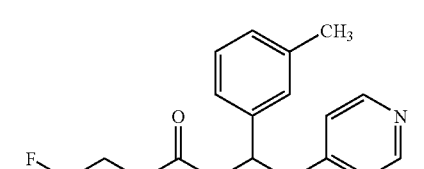 | 341 | 0.44 | 37.7 | 1.1 | not active | |
| 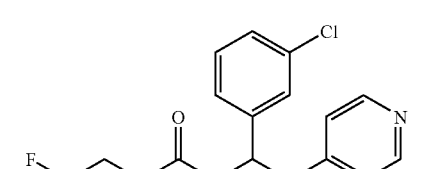 | 368 | 0.57 | 30.7 | 1.32 | not active | |
| 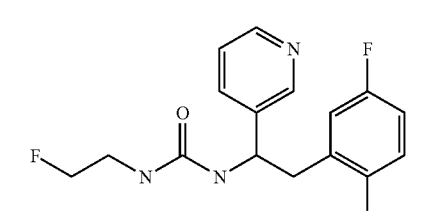 | not active | | 611 | 1.02 | not active | |

-continued

| Compound | Alpha 2A | | Alpha 2B | | Alpha 2C | |
|---|---|---|---|---|---|---|
| | EC$_{50}$ | IA | EC$_{50}$ | IA | EC$_{50}$ | IA |
| (3-methylphenyl, thiophen-2-yl urea structure) | not active | | 37 | 1.08 | not active | |
| (3-methylphenyl, thiophen-3-yl urea structure) | not active | | 63.4 | 1.0 | not active | |
| (3-chlorophenyl, 3-methylbenzyl urea structure) | 70.4 | 0.35 | 5.99 | 0.9 | not active | |
| (furan-2-yl, phenyl urea structure) | not active | | 513 | 0.77 | not active | |
| (3-methylphenyl, pyridin-2-yl urea structure) | not active | | 135 | 0.87 | not active | |
| (3-methylphenyl, pyridin-3-yl urea structure) | not active | | 53.2 | 0.95 | not active | |
| (3-fluorophenyl, 3-trifluoromethylphenyl urea structure) | not active | | 84.2 | 0.84 | not active | |

The hydrogen atoms which are present on the urea nitrogen atoms are omitted in the structures on the table.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is: ,

1. A compound of the formula

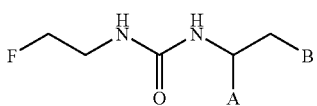

or a pharmaceutically acceptable salt thereof, a tautomer thereof, or a prodrug thereof;
wherein A is cycloalkyl, aryl, or heteroaryl;
A is a five-membered or six-membered monocyclic ring or a fused bicyclic thereof;
A is substituted or unsubstituted; and
if A is substituted, it has one or more stable substituents consisting of C, N, O, S, P, F, Cl, Br, and H; and
each substituent has 1, 2, 3, or 4 atoms which are not hydrogen; and
B is aryl or heteroaryl,
B is a five-membered or six-membered monocyclic ring or a fused bicyclic thereof;
B is substituted or unsubstituted; and
if B is substituted, it has one or more stable substituents consisting of C, N, O, S, P, F, Cl, Br, and H; and
each substituent has 1, 2, 3, or 4 atoms which are not hydrogen.

2. The compound of claim 1 wherein A is cyclohexyl, cyclopenyl, phenyl, thienyl, naphthyl, pyridinyl, or furyl and A is substituted or unsubstituted.

3. The compound of claim 2, wherein B is phenyl, pyridinyl, or thienyl, and B is substituted or unsubstituted.

4. The compound of claim 3 wherein A is substituted or unsubstituted, and if A is substituted, it has one or more substituents independently selected from Cl, F, $CF_3$, $OCH_3$, Br, $CH_3$, and OH.

5. The compound of claim 4, wherein B is substituted or unsubstituted, and if B is substituted, it has one or more substituents independently selected from Cl, F, $CF_3$, $OCH_3$, Br, $CH_3$, and OH.

6. The compound of claim 1 selected from the from the group consisting of
1-(1,2-diphenyl-ethyl)-3-(2-fluoro-ethyl)-urea;
1-[1-(3-chloro-phenyl)-2-phenyl-ethyl]-3-(2-fluoro-ethyl)-urea;
1-[1-(4-chloro-phenyl)-2-phenyl-ethyl]-3-(2-fluoro-ethyl)-urea;
1-(2-fluoro-ethyl)-3-[1-(3-fluoro-phenyl)-2-phenyl-ethyl]-urea;
1-(2-fluoro-ethyl)-3-[1-(3-methoxy-phenyl)-2-phenyl-ethyl]-urea;
1-(2-fluoro-ethyl)-3-[1-(4-fluoro-phenyl)-2-phenyl-ethyl]-urea;
1-[2-(2-Chloro-phenyl)-1-phenyl-ethyl]-3-(2-fluoro-ethyl)-urea;
1-(2-fluoro-ethyl)-3-[1-(2-fluoro-phenyl)-2-phenyl-ethyl]-urea;
1-(2-fluoroethyl)-3-[1-(4-methoxyphenyl)-2-phenyl-ethyl]urea;
1-(2-fluoroethyl)-3-[1-(2-methoxyphenyl)-2-phenyl-ethyl]urea;
1-[1-(3-Bromophenyl)-2-phenylethyl]-3-(2-fluoroethyl)urea;
1-(2-fluoroethyl)-3-[1-(4-methylphenyl)-2-phenylethyl]urea;
1-(2-fluoroethyl)-3-[1-(3-methylphenyl)-2-phenylethyl]urea;
1-[1-(3,4-dichlorophenyl)-2-phenylethyl]-3-(2-fluoroethyl)urea;
1-[1-(2-chlorophenyl)-2-phenylethyl]-3-(2-fluoroethyl)urea;
1-(1-cyclohexyl-2-phenylethyl)-3-(2-fluoroethyl)urea;
1-(1-cyclopentyl-2-phenylethyl)-3-(2-fluoroethyl)urea;
1-(2-fluoroethyl)-3-[2-(2-fluorophenyl)-1-phenylethyl]urea;
N-(2-fluoroethyl)-N'-[2-(3-fluorophenyl)-1-phenylethyl]urea;
1-(2-fluoroethyl)-3-[2-(4-fluorophenyl)-1-phenylethyl]urea;
1-[1-(3-chloro-2-fluorophenyl)-2-phenylethyl]-3-(2-fluoroethyl)urea;
1-(2-fluoroethyl)-3-[2-phenyl-1-(2-thienyl)ethyl]urea;
1-(2-fluoroethyl)-3-[1-(1-naphthyl)-2-phenylethyl]urea;
1-[1-(3-chlorophenyl)-2-(2-methylphenyl)ethyl]-3-(2-fluoroethyl)urea;
1-(2-fluoro-ethyl)-3-[2-(2-fluoro-phenyl)-1-m-tolyl-ethyl]-urea;
1-(2-fluoroethyl)-3-[2-(3-fluorophenyl)-1-m-tolylethyl]urea;
1-(2-fluoroethyl)-3-[2-(4-fluorophenyl)-1-m-tolylethyl]urea;
1-(2-fluoro-ethyl)-3-[1-(4-hydroxy-phenyl)-2-phenyl-ethyl]-urea;
1-[2-(2,5-difluoro-phenyl)-1-m-tolyl-ethyl]-3-(2-fluoro-ethyl)-urea;
1-[2-(2,3-difluoro-phenyl)-1-m-tolyl-ethyl]-3-(2-fluoro-ethyl)-urea;
1-(2-fluoro-ethyl)-3-[2-(2-fluoro-phenyl)-pyridin-3-yl-ethyl]-urea;
1-(2-fluoro-ethyl)-3-[2-(3-fluoro-phenyl)-1-pyridin-3-yl-ethyl]-urea;
1-(2-fluoro-ethyl)-3-[2-(4-fluoro-phenyl)-1-pyridin-3-yl-ethyl]-urea;
1-(2-fluoro-ethyl)-3-[2-(2-fluoro-phenyl)-1-pyridin-4-yl-ethyl]-urea;
1-[2-(3,4-difluoro-phenyl)-1-pyridin-4-yl-ethyl]-3-(2-fluoro-ethyl)-urea;
1-(2-fluoro-ethyl)-3-(2-pyridin-4-yl-1-m-tolyl-ethyl)-urea;
1-[1-(3-chloro-phenyl)-2-pyridin-4-yl-ethyl]-3-(2-fluoro-ethyl)-urea;
1-[2-(2,5-difluoro-phenyl)-1-pyridin-3-yl-ethyl]-3-(2-fluoro-ethyl)-urea;
1-(2-fluoro-ethyl)-3-(2-thiophen-2-yl-1-m-tolyl-ethyl)-urea;
1-(2-fluoro-ethyl)-3-(2-thiophen-2-yl-1-m-tolyl-ethyl)-urea;

1-[1-(3-chloro-phenyl)-2-m-tolyl-ethyl]-3-(2-fluoro-ethyl)-urea;
1-(2-fluoro-ethyl)-3-(1-furan-2-yl-2-phenyl-ethyl)-urea;
1-(2-fluoro-ethyl)-3-(2-pyridin-2-yl-1-m-tolyl-ethyl)-urea;
1-(2-fluoro-ethyl)-3-(2-pyridin-3-yl-1-m-tolyl-ethyl)-urea; and
1-(2-fluoro-ethyl)-3-[2-(3-fluoro-phenyl)-1-(3-trifluoromethyl-phenyl)-ethyl]-urea; or a pharmaceutically acceptable salt, or a tautomer thereof.

7. The compound of claim 1 further represented by the formula

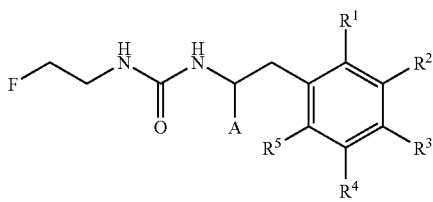

or a pharmaceutically acceptable salt thereof, a tautomer thereof, or a prodrug thereof;
wherein $R^1$, $R^2$, $R^3$, $R^4$, and $R^5$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

8. The compound of claim 1, further represented by the formula

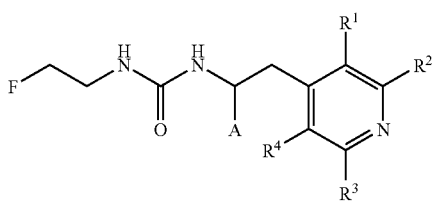

or a pharmaceutically acceptable salt thereof, a tautomer thereof, or a prodrug thereof;
wherein $R^1$, $R^2$, $R^3$, and $R^4$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

9. The compound of claim 1, further represented by the formula

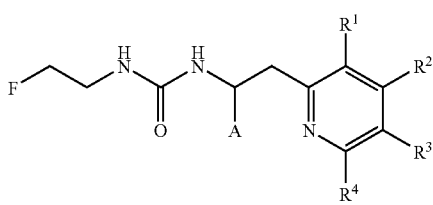

or a pharmaceutically acceptable salt thereof, a tautomer thereof, or a prodrug thereof;
wherein $R^1$, $R^2$, $R^3$, and $R^4$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

10. The compound of claim 1, further represented by the formula

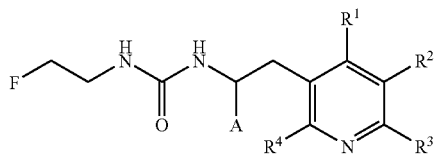

or a pharmaceutically acceptable salt thereof, a tautomer thereof, or a prodrug thereof;
wherein $R^1$, $R^2$, $R^3$, and $R^4$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

11. The compound of claim 1, further represented by the formula 20 or a pharmaceutically acceptable salt thereof, a tautomer thereof, or a prodrug thereof;

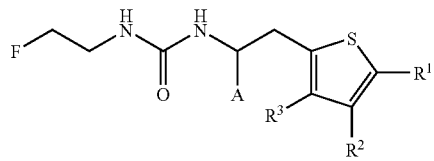

wherein $R^1$, $R^2$ and $R^3$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

12. The compound of claim 1, further represented by the formula

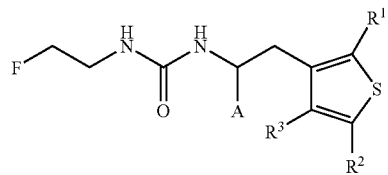

or a pharmaceutically acceptable salt thereof, a tautomer thereof, or a prodrug thereof;
wherein $R^1$, $R^2$, and $R^3$ are independently Cl, F, $CF_3$, O-methyl, O-ethyl, O-n-propyl, O-isopropyl, Br, methyl, ethyl, n-propyl, isopropyl, n-butyl, sec-butyl, isobutyl, t-butyl, OH, or $NO_2$.

13. A method comprising administering to a mammal a therapeutically effective amount of a compound of claim 1 for the treatment of chronic pain.

14. The method of claim 13, wherein the chronic pain is associated with allodynia.

15. The method of claim 13, wherein the chronic pain is associated with muscle spasticity.

16. The method of claim 13, wherein the chronic pain is associated with diarrhea.

17. The method of claim 13, wherein the chronic pain is neuropathic pain.

18. The method of claim 13, wherein the chronic pain is visceral pain.

19. A composition comprising a compound of claim 1.

* * * * *